United States Patent [19]

Morishita et al.

[11] Patent Number: 5,382,687
[45] Date of Patent: Jan. 17, 1995

[54] ENAMINE DERIVATIVES

[75] Inventors: Yoshii Morishita; Shigeru Hayashida; Yasushi Sugimoto, all of Hitachi; Hiroko Ishikawa, Katsuta; Hiroshi Kobayashi, Chikushino; Takaaki Sonoda, Fukuoka, all of Japan

[73] Assignee: Hitachi Chemical Company Ltd., Tokyo, Japan

[21] Appl. No.: 100,164

[22] Filed: Aug. 2, 1993

Related U.S. Application Data

[62] Division of Ser. No. 672,867, Mar. 20, 1991, abandoned.

[30] Foreign Application Priority Data

Mar. 20, 1990 [JP] Japan ................................. 2-70859
May 21, 1990 [JP] Japan ................................. 2-130806

[51] Int. Cl.$^6$ ................. G07C 211/50; C07C 217/54; C07C 217/80

[52] U.S. Cl. ..................... 564/319; 544/392; 544/394; 544/396; 546/206; 546/229; 546/232; 546/236; 546/304; 546/312; 548/420; 548/439

[58] Field of Search ............. 564/319; 544/392, 394, 544/396; 546/206, 236, 229, 232, 304, 312; 548/439, 420

[56] References Cited

U.S. PATENT DOCUMENTS 4,810,609 3/1989 Ueda ........................... 430/83
5,233,089 8/1993 Katsuya et al. ................ 564/319

Primary Examiner—Richard L. Raymond
Attorney, Agent, or Firm—Antonelli, Terry, Stout & Kraus

[57] ABSTRACT

An enamine derivative containing a fluoroalkyl group, a fluoroaryl group or a fluoroaralkyl group is effective as a charge transport material in an electrophotographic member excellent in sensitivity, residual potential, durability and the like electrophotographic properties.

4 Claims, 16 Drawing Sheets

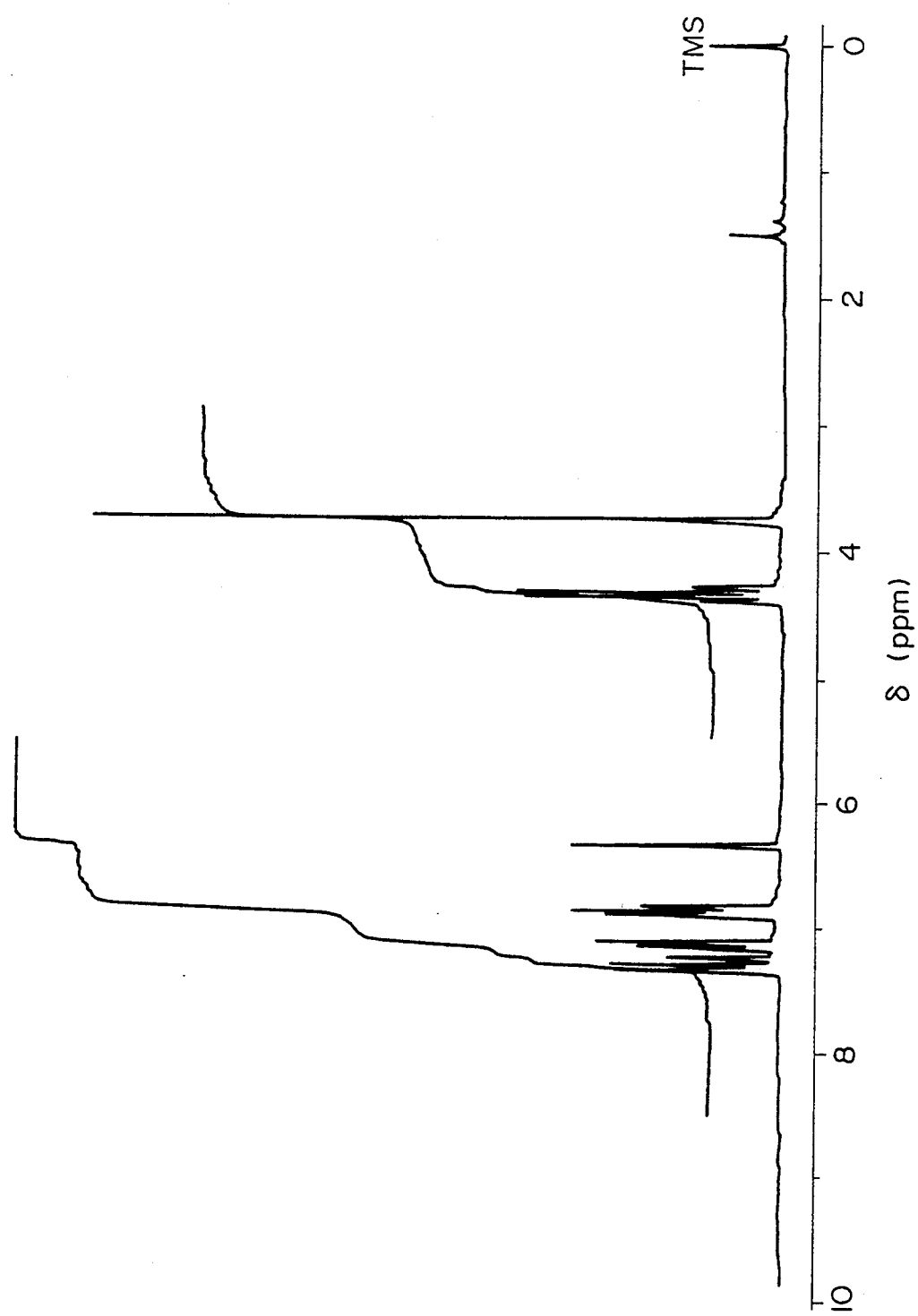
F I G. 4

ENAMINE DERIVATIVES

This application is a Divisional application of application Ser. No. 672,867, filed Mar. 20, 1991, now U.S. Pat. No. 5,272,030.

BACKGROUND OF THE INVENTION

This invention relates to enamine derivatives, precursors thereof, processes for producing the same and an electrophotographic member containing such enamine derivatives, There have been known enamine derivatives having various substituents [e.g. J. Imaging Science 29, pp. 7-10 (1985), Japanese Patent Unexamined Publication Nos. 62-237458, 62-244061, etc.]. These compounds are used as a charge transport material mainly in a charge transport layer of electrophotographic member for copying machines and laser beam printers. The charge transport layer is generally formed by coating a coating solution for charge transport layer prepared by mixing a charge transport material, a binder and a solvent for dissolution on a substrate using an applicator. In order to obtain a practically usable film thickness of 15 μm to 25 μm of the charge transport layer, it is generally necessary to make the total solid content (a total of a charge transport material and a binder) in the coating solution for charge transport layer about 15 to 20% by weight. Further, in order to obtain excellent electrophotographic properties, it is effective to enhance the mixing ratio of the charge transport material to the binder.

But known enamine derivatives have problems in solubility in solvents and/or compatibility with binders. For example, 1,1-bis(p-ethoxyphenyl)-2-[N,N-bis-(4-methoxyphenyl)amine] is relatively excellent in solubility in solvents compared with known enamine derivatives. When this compound is mixed with a binder of bisphenol A type polycarbonate (Lexan 141, a trade name, mfd. by General Electric Company) in an amount of 35% by weight per total solid content to prepare a coating solution for charge transport layer and to form a charge transport layer, the resulting charge transport layer seems to have good compatibility of the enamine compound with the polycarbonate resin in appearance. But when this layer is peeled off and subjected to differential scanning calorimetry, the glass transition point of the layer and that of the binder appear separately as shown in FIG. 15. This means that the polycarbonate resin and the enamine compound are phase separated microscopically and not compatible in the layer. An electrophotographic member containing such a charge transport layer which is phase separated microscopically has defects in that electrophotographic properties are lowered, particularly residual potential is undesirably raised.

SUMMARY OF THE INVENTION

It is an object of the present invention to provide enamine derivatives having fluorine atoms in substituents and excellent in solubility in solvents and compatibility with binders, overcoming the problems mentioned above. It is another object of the present invention to provide precursors of these enamine derivatives, processes for producing these enamine derivatives and precursors thereof. It is a further object of the present invention to provide an electrophotographic member containing such an enamine derivative and having excellent electrophotographic properties.

The present invention provides an enamine derivative of the formula:

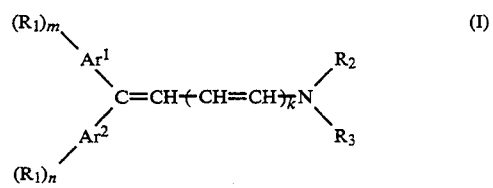

wherein $R_1$ is a fluorine-containing group of the formula: RfO— or $(Rf)_2N$—; Rf is a fluoroalkyl group, a fluoroaryl group or a fluoroaralkyl group; a plurality of $R_1$ may be the same or different; $R_2$ and $R_3$ are independently a non-substituted or substituted alkyl group, a non-substituted or substituted aryl group, a non-substituted or substituted aralkyl group, a non-substituted or substituted alicyclic group, a non-substituted or substituted heterocyclic group, or a residual group necessary for forming a 5-membered or 6-membered ring by bonding $R_2$ and $R_3$; $Ar^1$ and $Ar^2$ are independently an aryl group which may have one or more substituents other than $R_1$ or an arylene group which may have one or more substituents other than $R_1$; k is zero or an integer of 1; and m and n are independently zero or an integer of 1 to 3, provided that m and n cannot be zero at the same time.

The present invention also provides precursors of the enamine derivatives of the formula (I).

The present invention further provides a process for producing an enamine derivative of the formula (I), which comprises reacting an acetaldehyde derivative of the formula:

wherein $R_1$, $Ar^1$, $Ar^2$, and k are as defined above, with a secondary amine of the formula:

wherein $R_2$ and $R_3$ are as defined above.

The present invention still further provides a process for producing an enamine derivative of the formula:

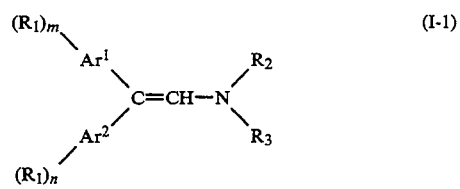

wherein $R_1$, $Ar^1$, $Ar^2$, $R_2$, $R_3$, m and n are as defined above, which comprises reacting a ketone derivative of the formula:

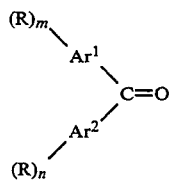

wherein R is a hydroxyl group or an amino group; $Ar^1$, $Ar^2$, m and n are as defined above, with a fluorine-containing Rf group introducing reagent, reacting the resulting ketone derivative of the formula:

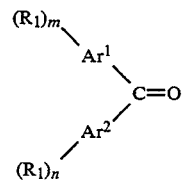

wherein $R_1$, $Ar^1$, $Ar^2$, m and n are as defined above, with an alkylidene triphenyl phosphorane, subjecting the resulting compound of the formula:

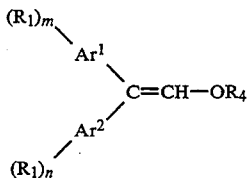

wherein $R_1$, $Ar^1$, $Ar^2$, m and n are as defined above; and $R_4$ is a methyl group, an n-butyl group, a phenyl group or a p-tolyl group, to hydrolysis with an acid, and reacting the resulting compound of the formula:

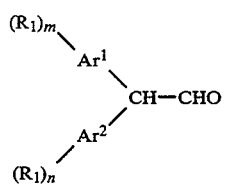

wherein $R_1$, $Ar^1$, $Ar^2$, m and n are as defined above, with a secondary amine of the formula (VII).

The present invention also provides a process for producing an enamine derivative of the formula:

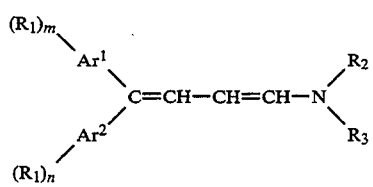

wherein $R_1$, $Ar^1$, $Ar^2$, $R_2$, $R_3$, m and n are as defined above, which comprises reacting a ketone derivative having a hydroxyl group or an amino group and represented by the formula:

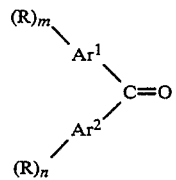

wherein R is a hydroxyl group or an amino group; $Ar^1$, $Ar^2$ m and n are as defined above with a fluorine-containing Rf group introducing reagent, reacting the resulting ketone derivative of the formula:

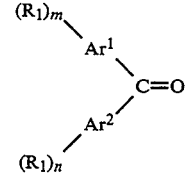

wherein $R_1$, $Ar^1$, $Ar^2$, m and n are as defined above, with an alkylidene triphenyl phosphorane, reacting the resulting ethylene derivative of the formula:

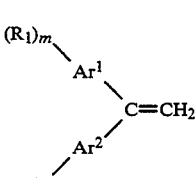

wherein $R_1$, $Ar^1$, $Ar^2$, m and n are as defined above, with a Vilsmeier reagent prepared from N,N-dimethylformamide (or N-methylformamide) and phosphoryl chloride, reacting the resulting acrolein derivative of the formula:

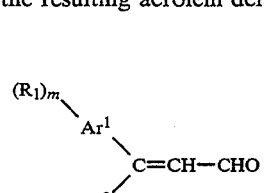

wherein $R_1$, $Ar^1$, $Ar^2$, m and n are as defined above, with an alkylidene triphenyl phosphorane, subjecting the resulting compound of the formula:

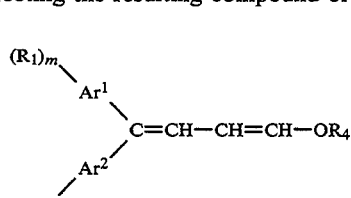

wherein $R_1$, $Ar^1$, $Ar^2$, $R_4$, m and n are as defined above, to hydrolysis with an acid, and reacting the resulting compound of the formula:

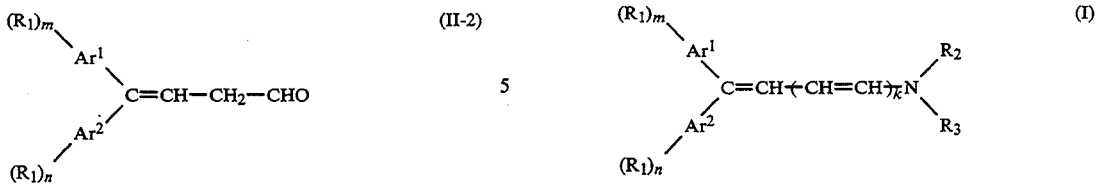

$$\begin{array}{c}(R_1)_m\\\phantom{xx}\diagdown\\\phantom{xxx}Ar^1\\\phantom{xxxx}\diagdown\\\phantom{xxxxx}C=CH-CH_2-CHO\\\phantom{xxxx}\diagup\\\phantom{xxx}Ar^2\\\phantom{xx}\diagup\\(R_1)_n\end{array}\quad(II\text{-}2)$$

wherein $R_1$, $Ar^1$, $Ar^2$, m and n are as defined above, with a secondary amine of the formula (VII).

The present invention further provide an electrophotographic member containing the enamine derivative of the formula (I).

BRIEF DESCRIPTION OF THE DRAWING

FIG. 4 is a $^1$H-NMR spectrum of 1,1-bis(p-2,2,2-trifluoroethoxyphenyl)-methoxyethylene.

DESCRIPTION OF THE PREFERRED EMBODIMENTS

Figure 1:
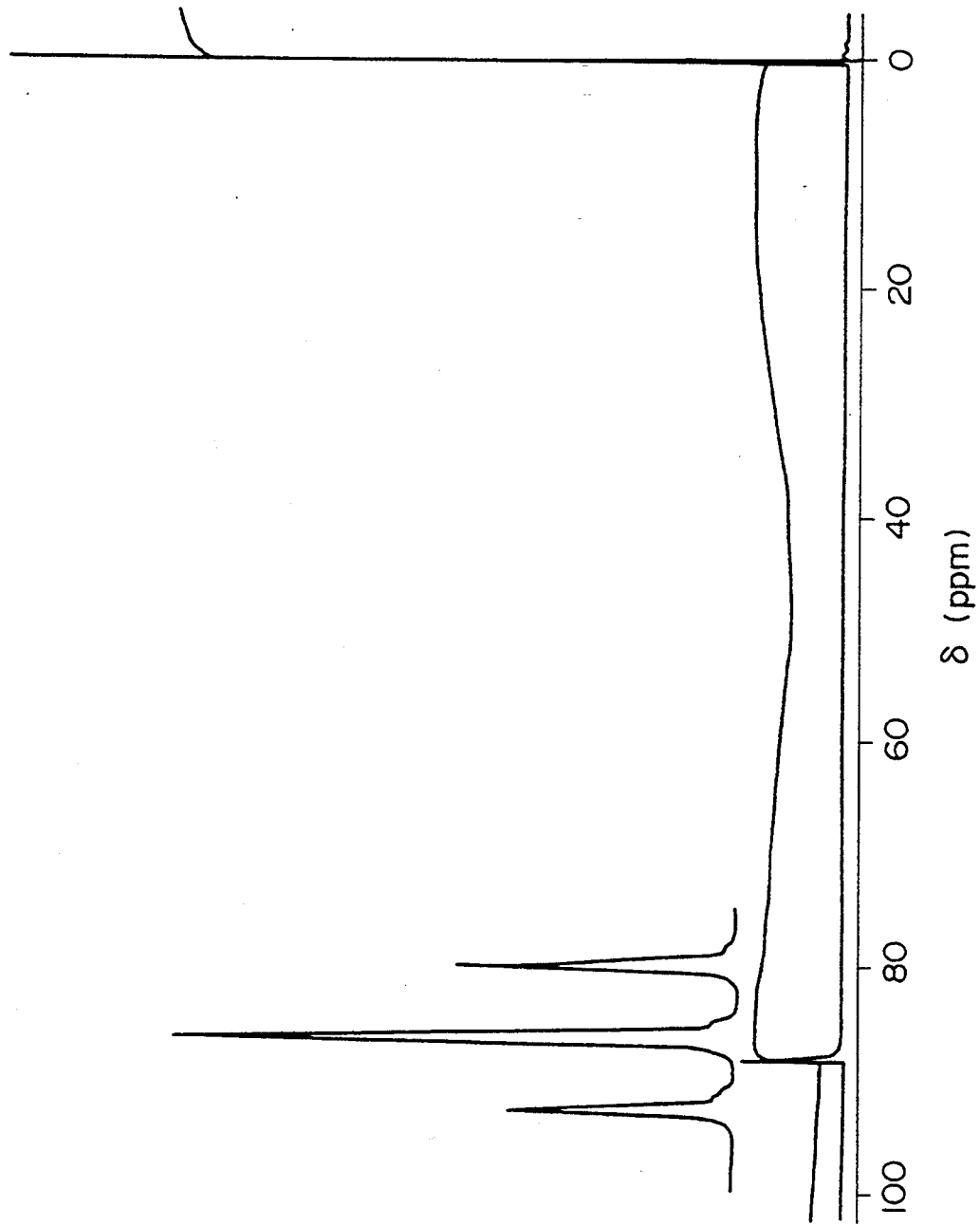
FIG. 1 is a $^{19}$F-NMR spectrum of 4,4'-bis(2,2,2-trifluoroethoxy)benzophenone.

The enamine derivative of the present invention is represented by the formula:

wherein $R_1$ is a fluorine-containing group of the formula: RfO— or $(Rf)_2N$—; Rf is a fluoroalkyl group, a fluoroaryl group or a fluoroaralkyl group; a plurality of $R_1$ may be the same or different; $R_2$ and $R_3$ are independently a non-substituted or substituted alkyl group, a non-substituted or substituted aryl group, a non-substituted or substituted aralkyl group, a non-substituted or substituted alicyclic group, a non-substituted or substituted heterocyclic group, or a residual group necessary for forming a 5-membered or 6-membered ring by bonding $R_2$ and $R_3$; $Ar^1$ and $Ar^2$ are independently an aryl group or arylene group which may have one or more substituents other than $R_1$; k is zero or an integer of 1; and m and n are independently zero or an integer of 1 to 3, provided that m and n cannot be zero at the same time.

In the definition of Rf, the fluoroalkyl group, the fluoroaryl group, and the fluoroaralkyl group mean a group wherein one or more hydrogen atoms in an alkyl group, an aryl group and an aralkyl group containing only carbon and hydrogen atoms are substituted with one or more fluorine atoms (a group of type A); a group wherein one or more hydrogen atoms in an alkyl group, an aryl group and an aralkyl group containing only carbon and hydrogen atoms are substituted with one or more type A groups; and a group wherein one or more hydrogen atoms of a type A group are substituted with one or more type A groups.

The alkyl group containing only carbon and hydrogen atoms includes a methyl group, an ethyl group, an n-propyl group, an isopropyl group, an n-butyl group, an isobutyl group, a tert-butyl group, a pentyl group, a hexyl group, a heptyl group, an octyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicocyl group, etc.

The aryl group containing only carbon and hydrogen atoms includes a phenyl group, a tolyl group, a xylyl group, an ethylphenyl group, a diethylphenyl group, a biphenyl group, a naphthylphenyl group, a naphthyl group, a methylnaphthyl group, a phenylnaphthyl group, an anthryl group, a methylanthryl group, a phenylanthryl group, a pyrenyl group, a methylpyrenyl group, a phenylpyrenyl group, etc.

The aralkyl group containing only carbon and hydrogen atoms includes a benzyl group, a methylbenzyl group, an ethylbenzyl group, a phenylethyl group, a naphthylmethyl group, a naphthylethyl group, etc.

In the definitions of $R_2$ and $R_3$, the alkyl group, the aryl group, the aralkyl group, the alicyclic group, the heterocyclic group and the residual group necessary for forming a 5-membered or 6-membered ring by combining $R_2$ and $R_3$, these groups being able to have one or more substituents, mean the alkyl group, the aryl group and aralkyl group containing only carbon and hydrogen atoms, and one or more hydrogen atoms in these groups being substituted with one or more substituents; the alicyclic group containing only carbon and hydrogen atoms, the heterocyclic group, one or more hydrogen atoms in these groups being substituted with one or more substituents; the residual group necessary for forming a 5-membered or 6-membered ring by bonding $R_2$ and $R_3$, one or more hydrogen atoms of the residual group being substituted with one or more substituents.

The alicyclic group containing only carbon and hydrogen atoms includes, for example, a cyclopentyl group, a methylcyclopentyl group, a cyclohexyl group, a methylcyclohexyl group, a norbornyl group, a methylnorbornyl group, a bicyclopentenyl group, a bicyclononyl group, a tricyclodecyl group, etc.

The heterocyclic group includes, for example, a pyridyl group, a quinolyl group, a carbazolyl group, an acridinyl group, an oxazolyl group, a furyl group, a thiofuryl group, a pyrrolyl group, a pyrazolinyl group, an imidazolyl group, an oxadiazolyl group, an indolyl group, a pyranyl group, a thiazolyl group, a pyrimidinyl group, a triazolyl group, a carbonyl group, a phenothiazinyl group, a quinoxalyl group, etc.

The residue necessary for forming a 5-membered or 6-membered ring by bonding $R_2$ and $R_3$ includes, for example,

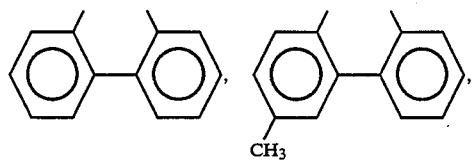

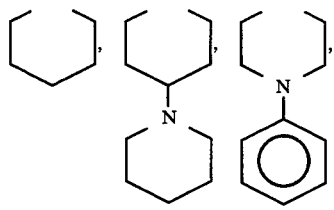

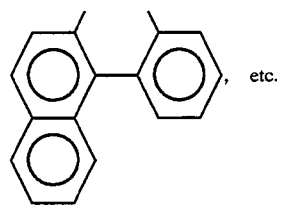

, etc.

As the substituents, there can be used a halogen atom, a cyano group, a nitro group, an amino group, a methyl group, an ethyl group, a propyl group, a butyl group, a pentyl group, a hexyl group, a heptyl group, an octyl group, a methoxy group, an ethoxy group, a propyloxy group, a butyloxy group, a pentyloxy group, a hexyloxy group, a heptyloxy group, an octyloxy group, a phenyloxy group, a dimethylamino group, a diethylamino group, a dipropylamino group, a dibutylamino group, a dioctylamino group, a diphenylamino group, a di(methylphenyl)amino group, a type A group mentioned above, etc.

The aryl group which may have one or more "substituents other than $R_1$" in the definitions of $Ar^1$ and $Ar^2$ includes the aryl group mentioned above containing only carbon and hydrogen atoms, and aryl groups wherein one or more hydrogen atoms are substituted with one or more substituents other than $R_1$.

The substituents other than $R_1$ include, for example, a halogen atom, a cyano group, a nitro group, an amino group, a methyl group, an ethyl group, a propyl group, a butyl group, a pentyl group, a hexyl group, a heptyl group, an octyl group, the type A group mentioned above, etc.

Examples of the arylene group are biphenylene, methyl biphenylene, ethyl biphenylene, t-butyl biphenylene, terphenylene, methyl terphenylene, ethyl terphenylene, t-butyl terphenylene, etc.

Preferable examples of the enamine derivatives of the formula (I) are as follows.

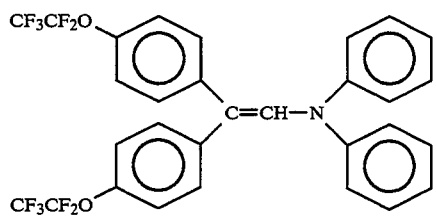

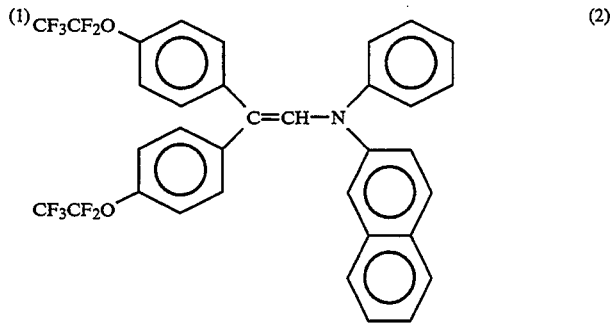

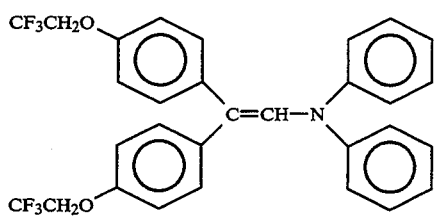

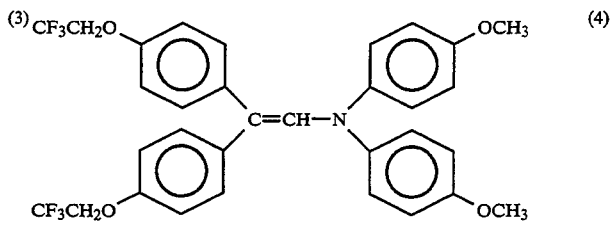

-continued
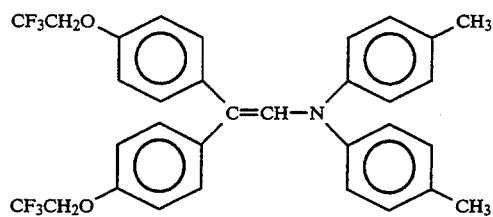
(5)
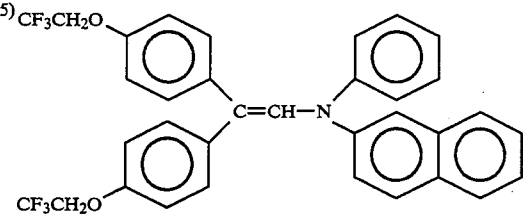
(6)
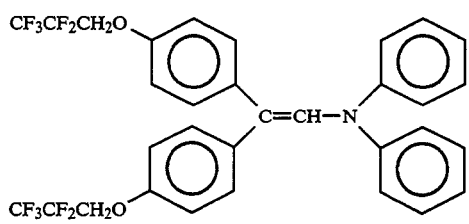
(7)
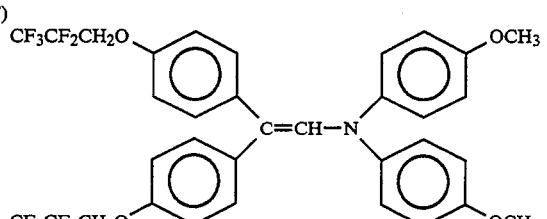
(8)
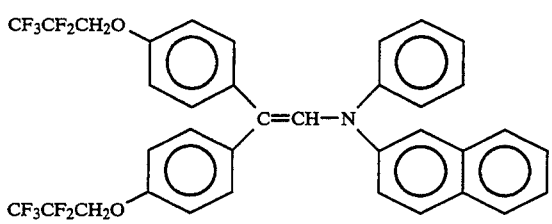
(9)
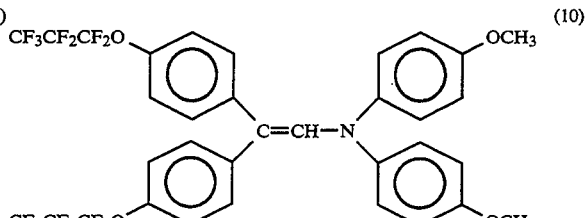
(10)
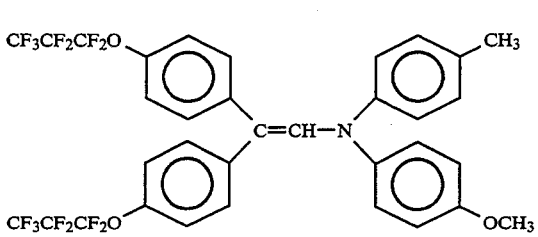
(11)
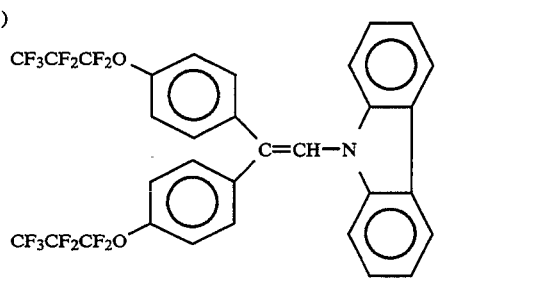
(12)
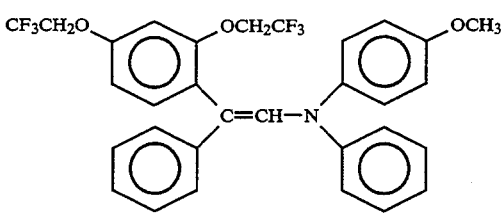
(13)
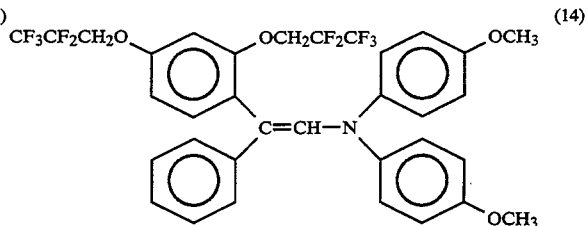
(14)
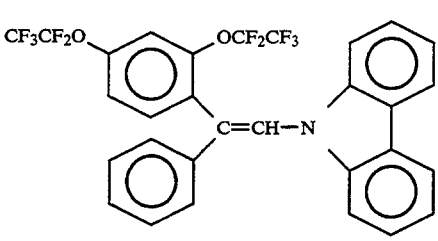
(15)
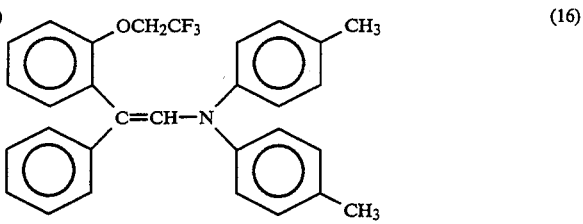
(16)
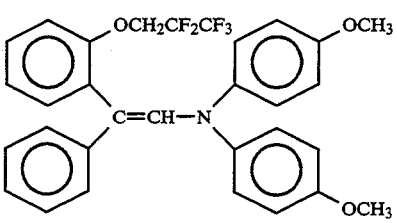
(17)
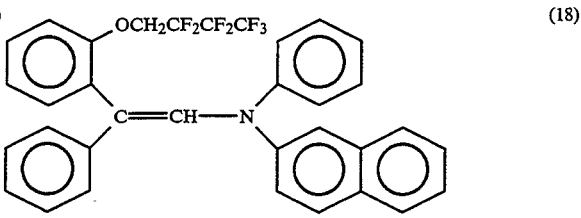
(18)

-continued
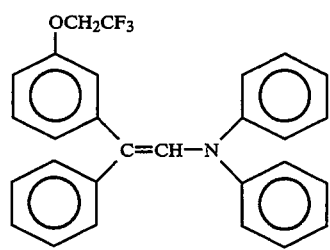 (19)
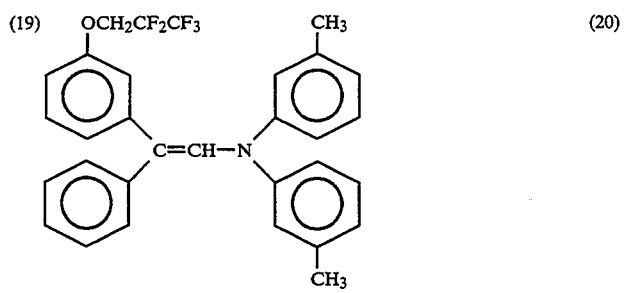 (20)
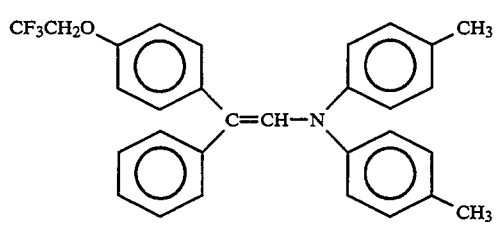 (21)
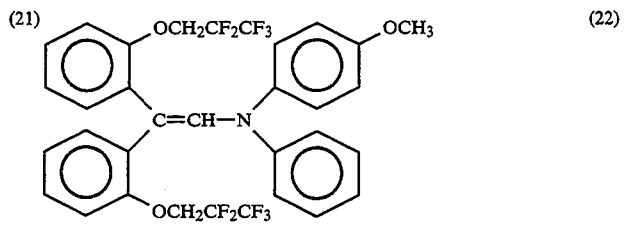 (22)
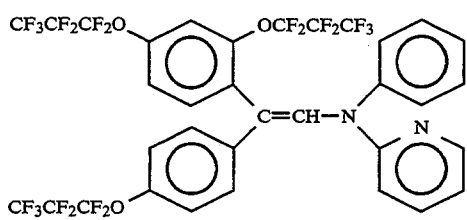 (23)
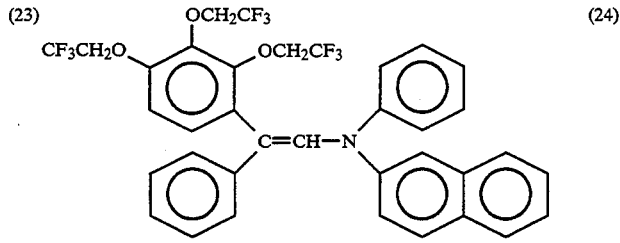 (24)
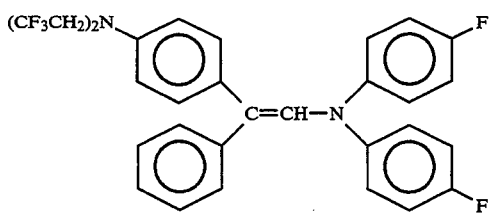 (25)
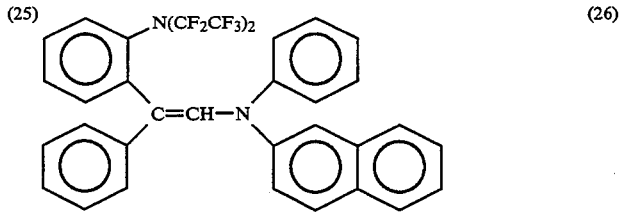 (26)
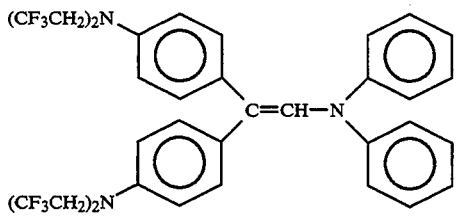 (27)
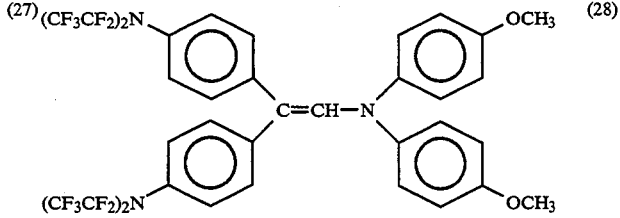 (28)
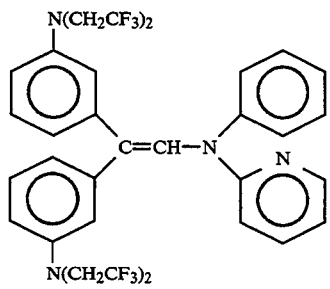 (29)
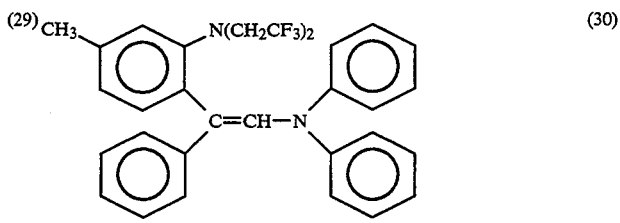 (30)

-continued
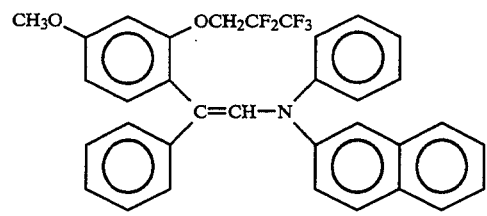(31)
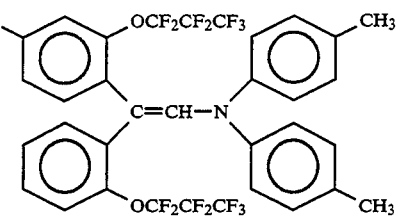(32)
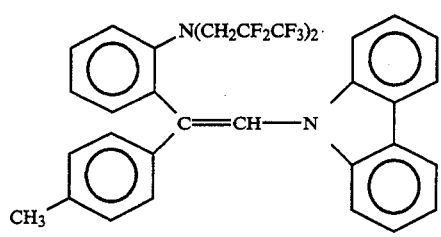
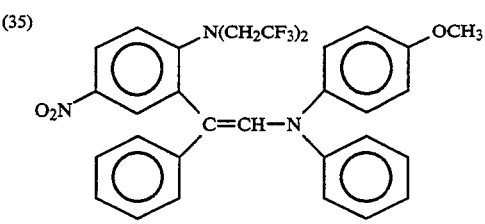(34)
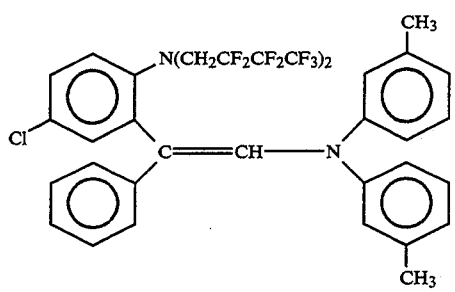(35)
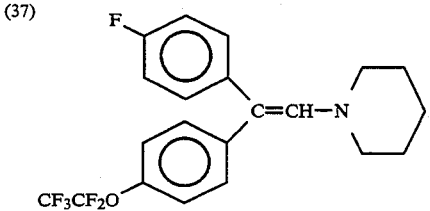(36)
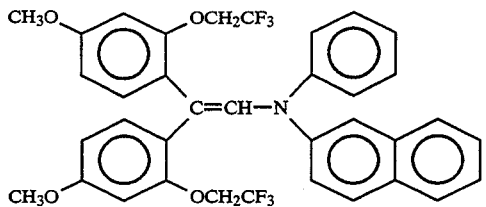(37)
(38)
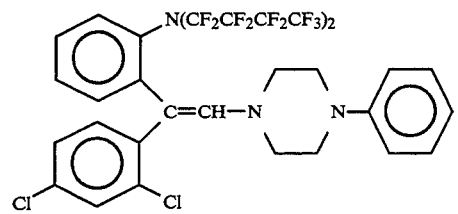(39)
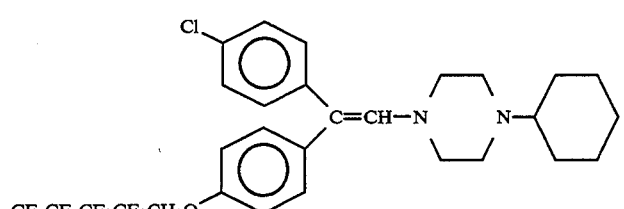(40)
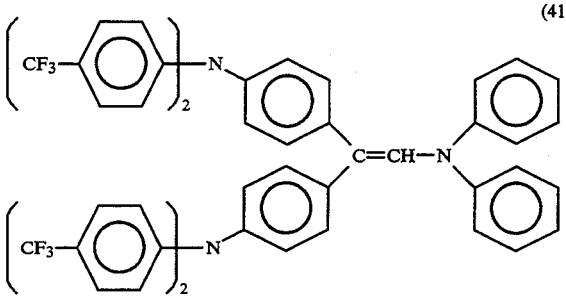(41)
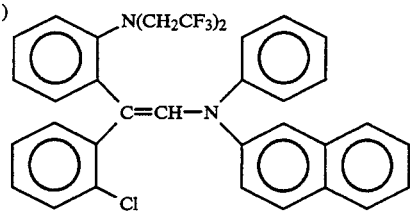(42)

-continued
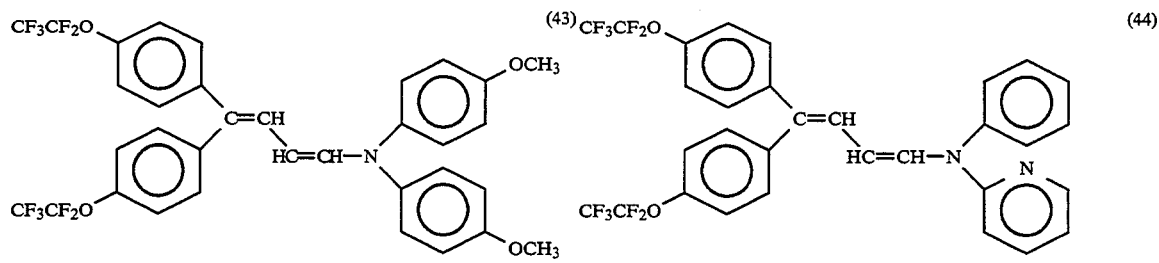
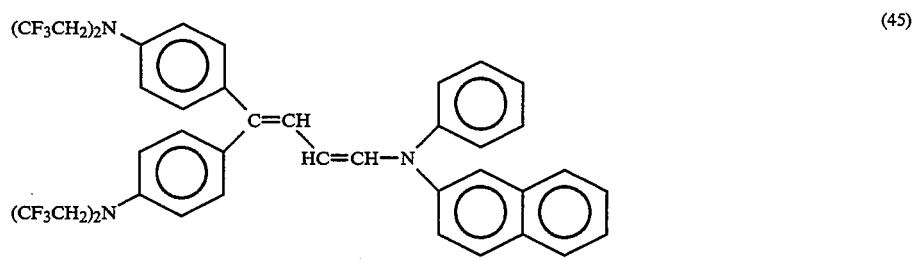
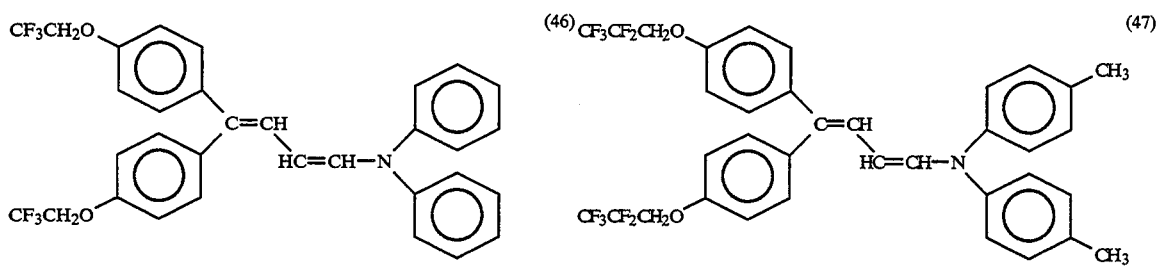
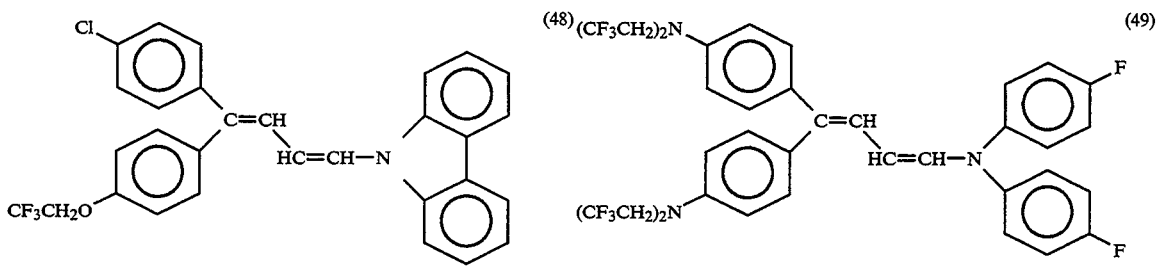
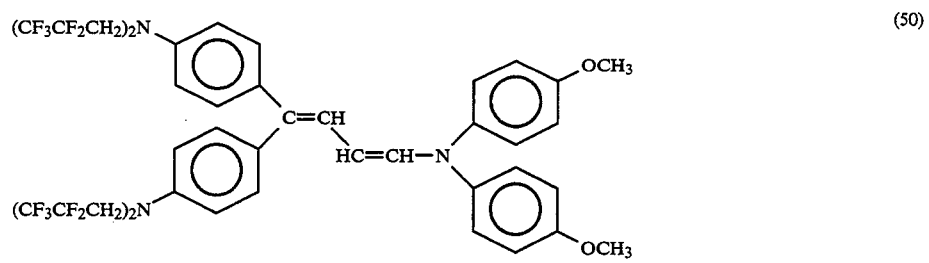
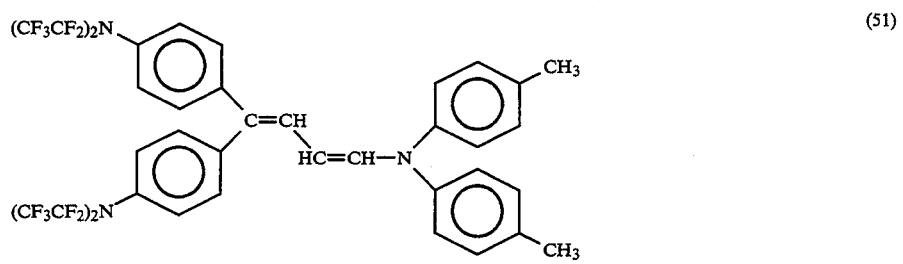

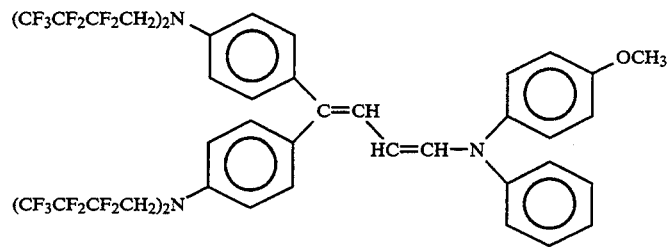
(52)
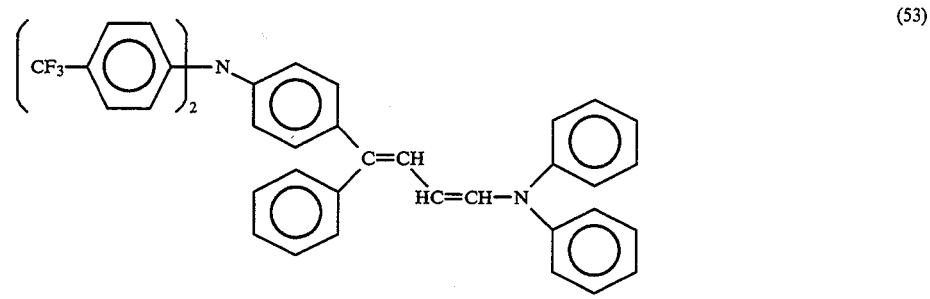
(53)
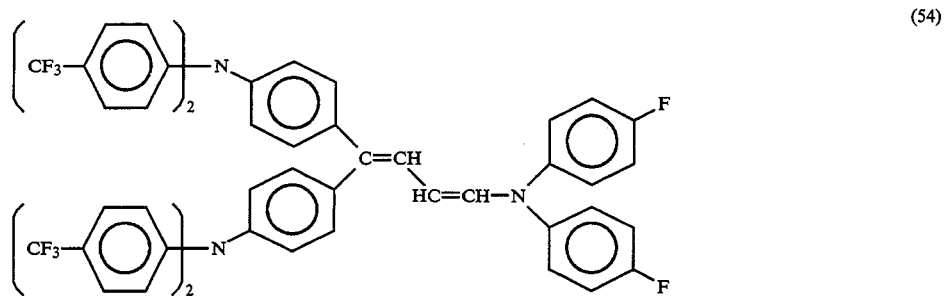
(54)
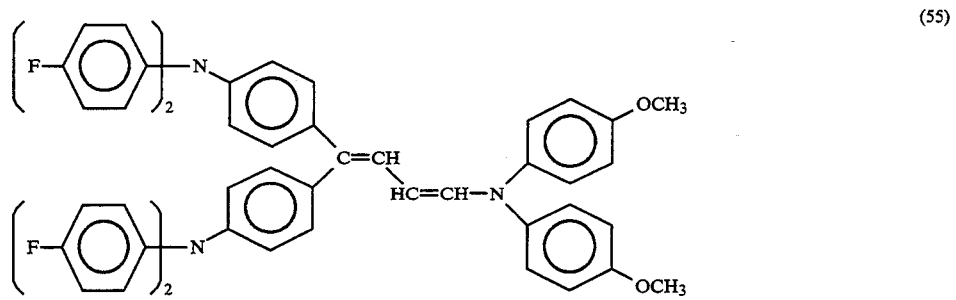
(55)
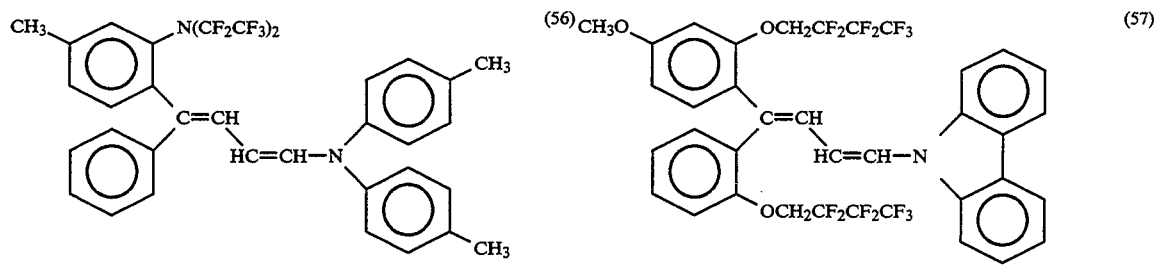
(56) (57)
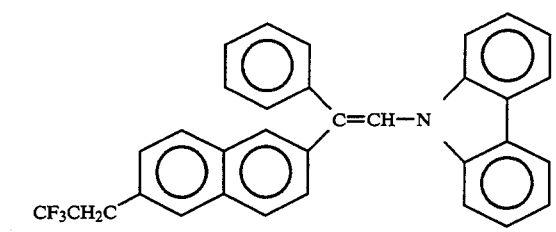
(58)

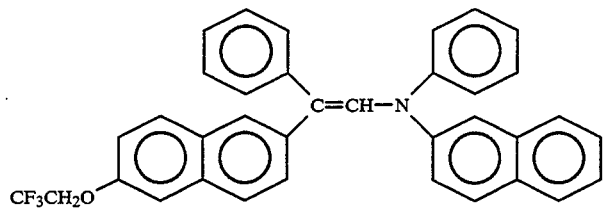
(59)
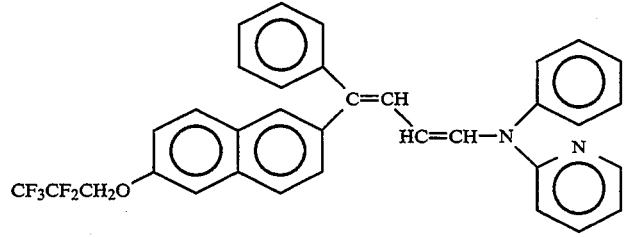
(60)
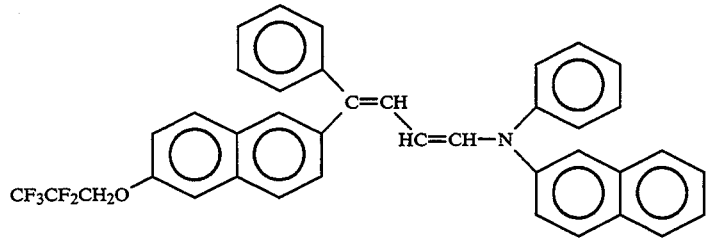
(61)
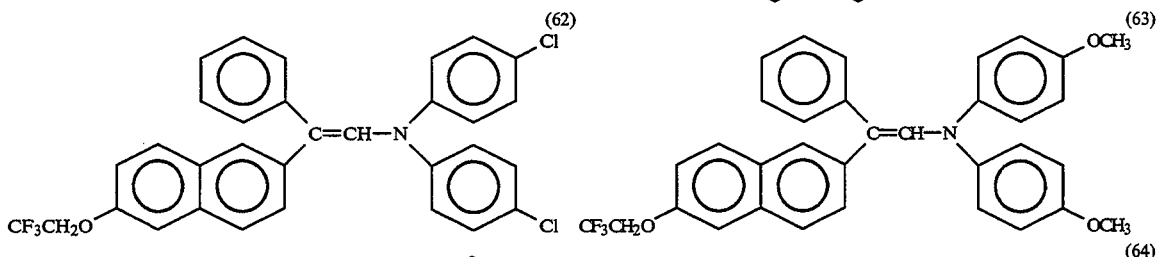
(62) (63)
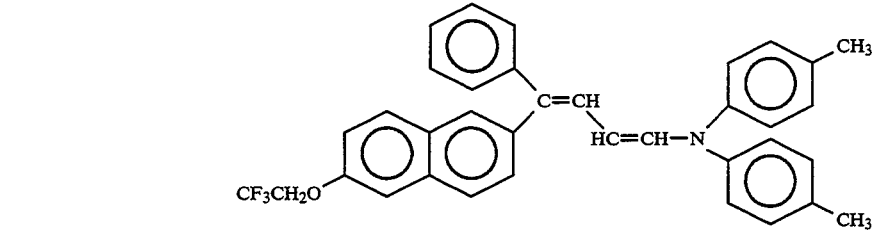
(64)
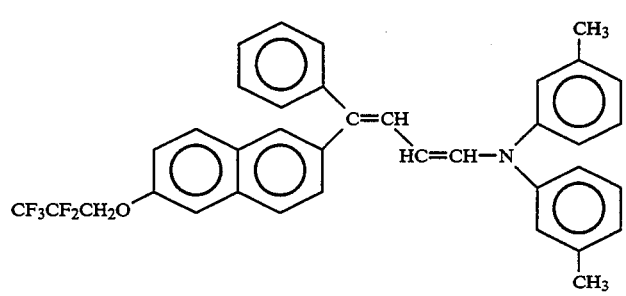
(65)
The enamine derivative of the formula (I) can be produced by reacting an acetaldehyde derivative of the formula:

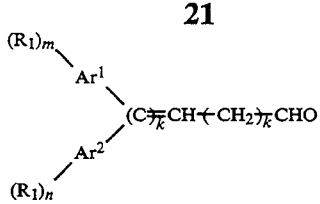  (II)

wherein $R_1$, $Ar^1$, $Ar^2$, and k are as defined above, with a secondary amine of the formula:

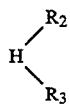  (VII)

wherein $R_2$ and $R_3$ are as defined above, in the presence of an acid catalyst in an organic solvent preferably at 80° C. to 160° C. for about 3 hours under reflux.

As the secondary amine of the formula (VII), there can be used dialkylamines such as dimethylamine, methylethylamine, diethylamine, etc., methylphenylamine, ethylphenylamine, diphenylamine, N-phenyl-1-naphthylamine, N-phenyl-2-naphthylamine, m,m'-ditolylamine, p,p'-ditolylamine, 4,4'-dimethoxydiphenylamine, 3-methyldiphenylamine, N-phenylbenzylamine, dibenzylamine, 3-methoxydiphenylamine, piperidine, 1-benzylpiperazine, 1-phenylpiperazine, 1,4-diformylpiperazine, 4-piperidinopiperidine, 4-benzylpiperidine, 1-phenylpiperidine, carbazole, indole, 5-bromoindole, pyrazole, 4-bromo-3,5-dimethylpyrazole, 9(10H)-acridone, 3-chlorodiphenylamine, 4,4'-dichlorodiphenylamine, 4,4'-difluorodiphenylamine, 2-anilinopyridine, etc.

As the acid catalyst, there can be used, for example, hydrochloric acid, sulfuric acid, acetic acid, trifluoroacetic acid, p-toluenesulfonic acid, etc.

As the organic solvent, there can be used benzene, toluene, xylene, etc.

It is preferable to use the secondary amine of the formula (VII) in an amount of 0.8 to 1.1 moles per mole of the acetaldehyde derivative of the formula (II).

The organic solvent is preferably used in an amount of 0.5 to 20 parts by weight per part by weight of the acetaldehyde derivative of the formula (II).

The acid catalyst is preferably used in an amount of 0.001 to 0.05 mole per mole of the acetaldehyde derivative of the formula (II).

The acetaldehyde derivative of the formula (II) can be synthesized by refluxing an enol ether derivative of the formula:

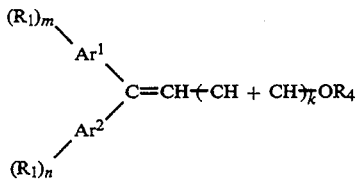  (III)

wherein $R_1$, $Ar^1$, $Ar^2$, m, n and k are as defined above; and $R_4$ is a methyl group, an n-butyl group, a phenyl group, or a p-tolyl group, in an acid with heating at 60° to 160° C. for 30 minutes to 5 hours.

As the acid, there can be used perchloric acid, acetic acid, sulfuric acid, hydrochloric acid, etc. in an amount of preferably 10 to 100 parts by weight per part by weight of the enol ether derivative of the formula (III).

The enol ether derivative of the formula (III) can be synthesized by reacting an alkylidene triphenyl phosphorane with a ketone derivative of the formula:

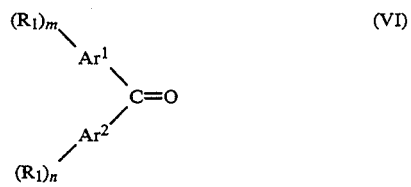  (VI)

wherein R $Ar^1$, $Ar^1$, $Ar^2$, m and n are as defined above, or an acrolein derivative of the formula:

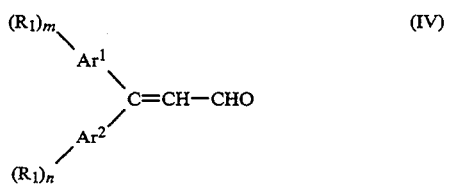  (IV)

wherein $R_1$, $Ar^1$, $Ar^2$, m and n are as defined above, in an organic solvent at a temperature of −50° to +70° C. for 0.5 to 5 hours (so-called Wittig reaction).

The alkylidene triphenyl phosphorane can be obtained by reacting a phosphonium salt with an basic compound. As the phosphonium salt, there can be used methoxymethyltriphenylphosphonium chloride, n-butoxy-methyltriphenylphosphonium chloride, phenoxymethyltriphenylphosphonium chloride, p-methylphenoxymethyltriphenylphosphonium chloride, etc. As the basic compound, there can be used n-butyllithium, phenyllithium, potassium butoxide, sodium methoxide, sodium ethoxide, sodium hydride, sodium triphenylmethane, etc.

As the organic solvent, there can be used diethyl ether, tetrahydrofuran, N,N-dimethylformamide, methanol, ethanol, n-butanol, benzene, xylene, etc.

The acrolein derivative of the formula (IV) can be synthesized by reacting an ethylene derivative of the formula:

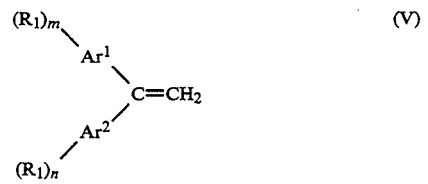  (V)

wherein $R_1$, $Ar^1$, $Ar^2$, m and n are as defined above, with a Vilsmeier reagent (so-called Vismeier reaction).

The Viismeier reagent can be prepared from N,N-dimethylformamide (or N-methylformanilide) and phospholyl chloride according to the method described in Helv. Chim. Acta 28, pp. 600–612 (1945) by H. Lovenz et al.

The ethylene derivative of the formula (V) can be synthesized by reacting a methylene triphenyl phosphorane with a ketone derivative of the formula (VI) in an organic solvent at −20° to +90° C., preferably at room temperature to 80° C. for 0.5 to 5 hours (so-called Wittig reaction).

The methylene triphenyl phosphorane can be obtained by reacting methyltriphenylphosphonium bromide with a basic compound such as n-butyllithium, phenyllithium, potassium butoxide, sodium methoxide, sodium ethoxide, sodium hydride, sodium triphenylmethane, etc.

The ketone derivative of the formula (VI) can be synthesized by reacting a ketone derivative of the formula:

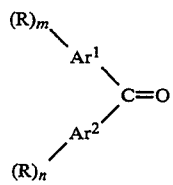 (VIII)

wherein R is a hydroxyl group or an amino group, with a fluorine-containing Rf group introducing reagent in an organic solvent in the presence of a basic compound at −78° to +90° C., preferably 0° to 50° C. for 5 minutes to 5 hours. The Rf group means a fluorine-containing substituent such as a fluoroalkyl group, a fluoroaryl group, a fluoroaralkyl group, etc.

As the organic solvent, there can be used n-pentane, n-hexane, methylene chloride, acetonitrile, diethyl ether, tetrahydrofuran, N,N-dimethylformamide, N,N-dimethylsulfoxide, hexamethylphosphoric triamide, sulfolane, etc.

As the basic compound used for the reaction, there can be used sodium carbonate, sodium hydrogen carbonate, sodium hydride, lithium hydride, pyridine, 2,6-di-t-butyl-4-methylpyridine, etc.

As the Rf group introducing reagent, there can be used fluoroalkylating agents such as (perfluoroalkyl)-phenyl iodonium trifluoromethane sulfonate, (1,1-dihydroperfluoroalkyl)phenyl iodinium trifluoromethane sulfonate, trifluoromethanesulfonic acid fluoroalkyl esters, perfluoroalkyl halides, 1,1-dihydroperfluoroalkyl halides, etc.

The fluoroalkylating agent mentioned above can easily be synthesized by the descriptions in J. Fluorine Chem. 31, pp. 37–56 (1986), J. Fluorine Chem. 28, pp. 235–239 (1985), and Tetrahedron, 2.1, pp. 1–4 (1965).

The Rf group introducing reagent and the basic compound can preferably be used in amounts of 0.8 to 1.5 chemical equivalents, respectively, per chemical equivalent of the functional group for introducing Rf group into the ketone derivative of the formula (VIII).

It is preferable to use the organic solvent in an amount of 0.5 to 10 parts by weight per part by weight of the ketone derivative of the formula (VIII).

Among the enamine derivatives of the formula (I), an enamine derivative of the formula:

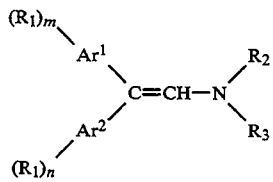 (I-1)

can be synthesized by
reacting a ketone derivative of the formula:

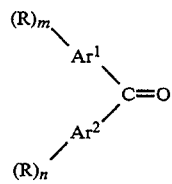 (VIII)

with a fluorine-containing Rf group introducing reagent, reacting the resulting ketone derivative of the formula:

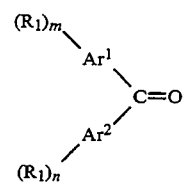 (VI)

with an alkylidene triphenyl phosphorane,
subjecting the resulting compound of the formula:

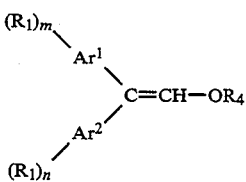 (III-1)

to hydrolysis with an acid, and
reacting the resulting compound of the formula:

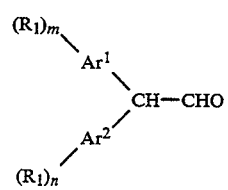 (II-1)

with a secondary amine of the formula:

 (VII)

Further, an enamine derivative of the formula:

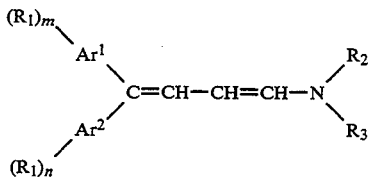 (I-2)

can be synthesized by
reacting a ketone derivative of the formula:

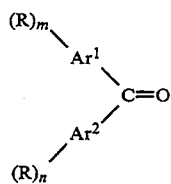
(VIII)

with a fluorine-containing Rf group introducing reagent, reacting the resulting ketone derivative of the formula:

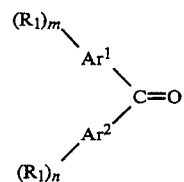
(VI)

with methylene triphenyl phosphorane, reacting the resulting ethylene derivative of the formula:

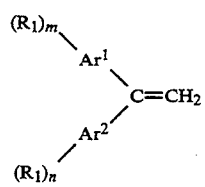
(V)

with a Viismeier reagent prepared from N,N-dimethylformamide or N-methylformanilide and phosphoryl chloride, reacting the resulting acrolein derivative of the formula:

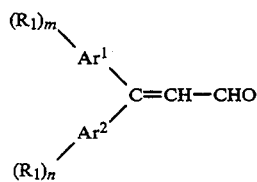
(IV)

with an alkylidene triphenyl phosphorane, subjecting the resulting compound of the formula:

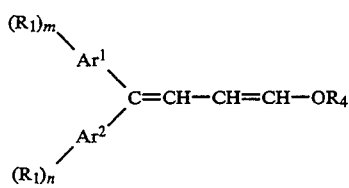
(III-2)

to hydrolysis with an acid, and reacting the resulting compound of the formula:

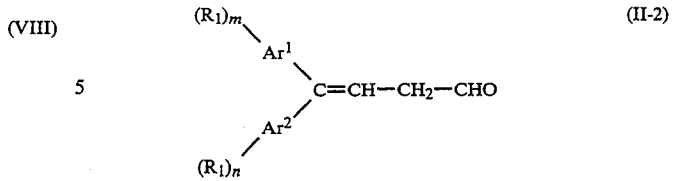
(II-2)

with a secondary amine of the formula:

(VII)

The enamine derivatives can be included in an electrophotographic member for functioning as a charge transport material. When applied to the electrophotographic member, the enamine derivatives of the formula (I) can be used together with other charge transport materials. Examples of other charge transport materials are high polymeric compounds such as poly-N-vinylcarbazole, halogenated poly-N-vinylcarbazole, polyvinylpyrene, polyvinylindroquinoxaline, polyvinylbenzothiophene, polyvinylanthracene, polyvinylacridine, polyvinylpyrazoline, etc.; low molecular weight compounds such as fluorene, fluorenone, 2,7-dinitro-9-fluorenone, 2,4,7-trinitro-9-fluorenone, 4H-indeno(1,2,6)thiophen4-one, 3,7-dinitro-dibenzothiophene-5-oxide, 1-bromopyrene, 2-phenylpyrene, carbazole, 3-phenylcarbazole, 2-phenylindole, 2-phenylnaphthalene, oxadiazole, triazole, 1-phenyl-3-(4-diethylaminostyryl)5-(4-diethylaminophenyl)pyrazoline, 2-phenyl-4-(4-diethylaminophenyl)-5-phenyloxazole triphenylamine, imidazole, chrysene, tetraphene, acridine, etc. Other charge transport material can be used preferably 1 part by weight or less, more preferably 0.25 part by weight or less per part by weight of the enamine derivative of the formula (I) in order to not damage the improvement in electrophotographic properties due to the enamine derivative of the formula (I).

The electrophotographic member of the present invention comprises a layer of a mixture of a charge transport material and a charge generation material formed on an electroconductive support in the case of a monolayer structure. It is possible to take a two-layer structure comprising a charge transport layer and a charge generation layer as a photoconductive layer formed on an electroconductive support.

As the charge generation material, there can be used Si, Se, $As_2S_3$, $Sb_2S_3$, $Sb_2Se_3$, CdS, CdSe, CdTe, ZnO, α-form, β-form, τ-form, X-form and the like various crystal type non-metallic phthalocyanine pigments; metallic phthalocyanine and naphthalocyanine pigments such as copper phthalocyanine, aluminum phthalocyanine, zinc phthalocyanine, titanyl phthalocyanine, cobalt phthalocyanine, etc.; azo pigments, anthraquinone pigments, indigoid pigments, quinacridone pigments, perylene pigments, polycyclic quinone pigments, squaric acid methine pigments, azulene pigments, pyrrolopyrrole pigments, etc. It is possible to use other pigments disclosed in Japanese Patent Unexamined Publication Nos. 47-37453, 47-37544, 47-18543, 47-18544, 48-43942, 48-70538, 49-1231, 49-105536, 50-75214, 50-92738, 61-162555, etc.

In the photoconductive layer, there can be used conventionally used additives such as a binder, a plasticizer, a fluidity imparting agent, a pin-hall inhibiting agent, etc.

As the binder, there can be used linear saturated polyester resins, polycarbonate resins, acrylic resins, butyral resins, polyketone resins, polyurethane resins, poly(N-vinylcarbazole), poly(p-vinylphenyl)anthracene, silicone resins, polyamide resins, epoxy resins, polystyrene resins, etc. Further, as the binder, it is possible to use thermosetting and photo-curable resins which can be crosslinked by heat and/or light. Such resins are not particularly limited so long as the resins have insulating properties and have film-forming ability at normal state and/or the resins can form films by curing by light.

As the plasticizer, there can be used halogenated paraffins, dimethyl naphthalene, dibutyl phthalate, etc.

As the fluidity imparting agent, there can be used Modaflow (mfd. by Monsanto Chemical Co.), Akulonal 4F (mfd. by BASF AG.), etc.

As the pin-hall inhibiting agent, there can be used benzoin, dimethyl terephthalate, etc.

These additives can be used in suitable amounts by properly selecting suitable compounds.

In the case of taking the mono-layer structure, it is preferable to use the charge transport material in an amount of 1 to 10 parts by weight, more preferably 1 to 5 parts by weight per part by weight of the charge generation material. The binder is preferably used in an amount of 1 to 3 parts by weight per part by weight of the charge generation material. When the amount of the binder is too much, there is a tendency to lower electrophotographic properties. The plasticizer and the like additives are generally used in amounts of several percents or less based on the weight of the charge generation material. The thickness of the photoconductive layer is usually 5 to 100 $\mu$m, said thickness being determined so as not to deteriorate photosensitivity, and charging characteristics.

On the other hand, when the two-layer structure is taken, the charge generation layer of Si or Se can be formed in 1 to 20 $\mu$m thick on the electroconductive support by vacuum deposition. In the case of using an inorganic material other than Si and Se, an organic metal pigment or an organic pigment, as the charge generation material, it is necessary to use the binder mentioned above in order to form a film. The binder is usually used in an amount of 1 to 3 parts by weight per part by weight of the charge generation material. When the amount is larger than 3 parts by weight, there is a tendency to lower electrophotographic properties. The plasticizer and the like additives are generally used in amounts of several percents or less based on the weight of the charge generation material.

As to the charge transport layer, when the enamine derivative of the formula (I) is used alone as the charge transport material, the binder is used in an amount of 0.5 to 3 parts by weight per part by weight of the charge transport material due to good compatibility of the charge transport material with the binder. In the case of using other charge transport materials together, it is not necessary to use the binder when a polymeric compound is used as the charge transport material, but the binder can be used in an amount of 3 parts by weight or less per part by weight of the polymeric compound. When the amount is larger than 3 parts by weight, there is a tendency to lower electrophotographic properties. On the other hand, when a low molecular weight compound is used together as the charge transport material, the binder is usually used in an amount of 0.3 to 3 parts by weight per part by weight of a total of the enamine derivative of the formula (I) and the low molecular weight compound. When the amount is too small, the formation of the charge transport layer often becomes difficult, while when the amount is too large, there is a tendency to lower electrophotographic properties. The plasticizer and the like additives are optionally used in amounts of 0.05 part by weight or less per part by weight of the charge transport material.

The thickness of the charge generation layer is generally 0.01 to 10 $\mu$m, preferably 0.1 to 5 $\mu$m. When the thickness is less than 0.01 $\mu$m, it becomes often difficult to make the thickness of charge generation layer uniform, On the other hand, when the thickness is larger than 10 $\mu$m, there is a tendency to lower electrophotographic properties. The thickness of the charge transport layer is usually 5 to 50 $\mu$m, preferably 10 to 25 $\mu$m. When the thickness is less than 5 $\mu$m, the initial potential is easily lowered, while when the thickness is larger than 50 $\mu$m, there is a tendency to lower the sensitivity.

In any cases, the thicknesses are desirably decided so as not to deteriorate the photosensitivity, and charging characteristics. It should be noted that when the thickness of the photoconductive layer is too large, there is a fear of lowering flexibility of the layer per se.

When the electrophotographic member takes the two-layer structure having the charge generation layer and the charge transport layer, it is preferable to form the charge generation layer on the electroconductive support, followed by formation of the charge transport layer thereon, considering electrophotographic properties. But it is possible to form the charge generation layer on the charge transport layer.

As the electroconductive support, there can be used metals such as aluminum, brass, copper, gold, etc., metal-deposited Mylar film, etc.

In order to form a mono-layer containing the charge generation material and charge transport material or two layers of the charge generation layer and the charge transport layer on the electroconductive support, the components for individual layers are dissolved or dispersed uniformly in a solvent, coated on the electroconductive support, followed by drying. As the solvent, there can be used ketones such as acetone, methyl ethyl ketone, etc., ethers such as tetrahydrofuran, etc., aromatic solvents such as toluene, xylene, etc. When the charge generation layer or the charge transport layer is formed first, and then the charge transport layer or the charge generating layer is formed thereon, the two-layer structure can be formed after drying.

Coating and drying can be carried out, for example, by forming a layer in predetermined thickness using a doctor blade, natural drying for 15 minutes, and drying with heating at 80° to 150° C. for 60 minutes.

The electrophotographic member can have an undercoating layer between the electroconductive support and the photoconductive layer. The undercoating layer can be formed using a thermoplastic resin. As the thermoplastic resin, there can be used polyamide resins, polymethane resins, polyvinyl butyral resins, melamine resins, casein resins, phenol resins, epoxy resins, ethylene-vinyl acetate copolymer resins, ethylene-acrylic acid copolymer resins, etc. Among these resins, polyamide resins are preferable. Polyamide resins are available commercially in trade names of Toresin MF30, Toresin F30, Toresin EF30T (mfd. by Teikoku Kagaku Sangyo K. K.), M-1276 (mfd. by Nihon Rilsan K. K.), etc. The resins contained in the undercoating layer can be used alone or as a mixture of two or more resins.

When the undercoating layer is formed by using a polyamide resin, it is preferable to use one or more thermosetting resins and a curing agent together with the polyamide resin. By the use of thermosetting resin and curing agent together, solvent resistance and film strength of the undercoating layer are improved so as to prevent the undercoating layer from damages caused by a solvent and the like in the solution for forming the photoconductive layer at the time of forming the photoconductive layer.

As the thermosetting resin, there can be used melamine resins, benzoguanamine resins, polymethane resins, epoxy resins, silicone resins, polyester resins, acrylic resins, urea resins, etc. Any thermosetting resins which can form films at normal state can be used. It is preferable to use the thermosetting resin in an amount of 300% by weight or less based on the weight of the thermoplastic resin.

As the curing agent, there can be used carboxylic acids such as trimellitic acid, pyromellitic acid, etc., an oligomer of an amide containing a carboxylic acid, etc. The curing agent can be used in an amount of 20% by weight or less based on the weight of the thermosetting resin.

The undercoating layer can be formed by preparing a solution uniformly dissolving a thermoplastic resin, and if necessary a thermosetting resin, a curing agent, etc. in a mixed solvent of an alcohol such as methanol, ethanol, isopropanol, etc. and a halogen series solvent such as methylene chloride, 1,1,2-trichloroethane, etc., coating the solution on the electroconductive support by a dip coating method, a spray coating method, a roll coating method, an applicator coating method, a wire bar coating method, etc., and drying.

The thickness of the undercoating layer is preferably 0.01 $\mu$m to 0.5 $\mu$m, more preferably 0.05 $\mu$m to 20 $\mu$m. When the thickness is to small, it is impossible to form a uniform charge generation layer, and there is a tendency to generate small black stains and small white stains. On the other hand, when the thickness is too large, accumulation of residual potential becomes large, and there is a tendency to lower the printed letter density with an increase of the number of sheets for printing.

Using the electrophotographic member of the present invention, copying can be carried out by a conventional method comprising applying charging and exposing to light on the surface, developing, transferring an image on plain paper and fixing.

The present invention is illustrated by way of the following Examples, in which all parts and percents are by weight, unless otherwise specified.

PRODUCTION EXAMPLE 1

In a 100-ml flask equipped with a stirrer, a thermometer, a nitrogen introducing pipe and a condenser, 50 ml (0.297 mol) of trifluoromethanesulfonic anhydride and 25 ml (0.342 mole) of 2,2,2-trifluoroethanol were placed at room temperature and stirred for 30 minutes in a nitrogen atmosphose, followed by reflux for 3 hours. After distillation, 50.3 g of 2,2,2-trifluoroethyl trifluoromethanesulfonate was obtained in yield of 73%.

CF$_3$CH$_2$OSO$_2$CF$_3$: colorless transparent liquid b.p. 87°–92° C. (90.5°–91° C.: reference disclosed value)

EXAMPLE 1

In a 200-ml flask similar to that used in Production Example 1, 80 ml of anhydrous DMF suspension of 6.5 g (0.217 mole) of 80% sodium hydroxide (oil dispersion) was placed and 17.63 g (82.3 mmoles) of 4,4'-dihydroxybenzophenone in 80 ml of anhydrous DMF was gradually added dropwise, followed by stirring for 1.5 hours. To the resulting yellow-white cake, 47.6 g (0.205 mole) of 2,2,2-trifluoroethyl trifluoromethanesulfonate was added dropwise in about 45 minutes. After dissolving the yellow-white cake, the resulting mixture was stirred for 1.5 hours. Then, the resulting solution was poured into 1.5 liters of distilled water, and made acidic with 5% hydrochloric acid. The resulting white precipitate was filtered and washed sufficiently with distilled water. After drying, the white precipitate was recrystallized from ethanol to yield 29.5 g of white needles of 4,4'-bis(2,2,2-trifluoroethoxy)benzophenone in yield of 95%.

| (2) Elementary analysis | | |
|---|---|---|
| | C (%) | H (%) |
| Calculated | 53.98 | 3.20 |
| Found | 53.97 | 3.10 |

Figure 2:
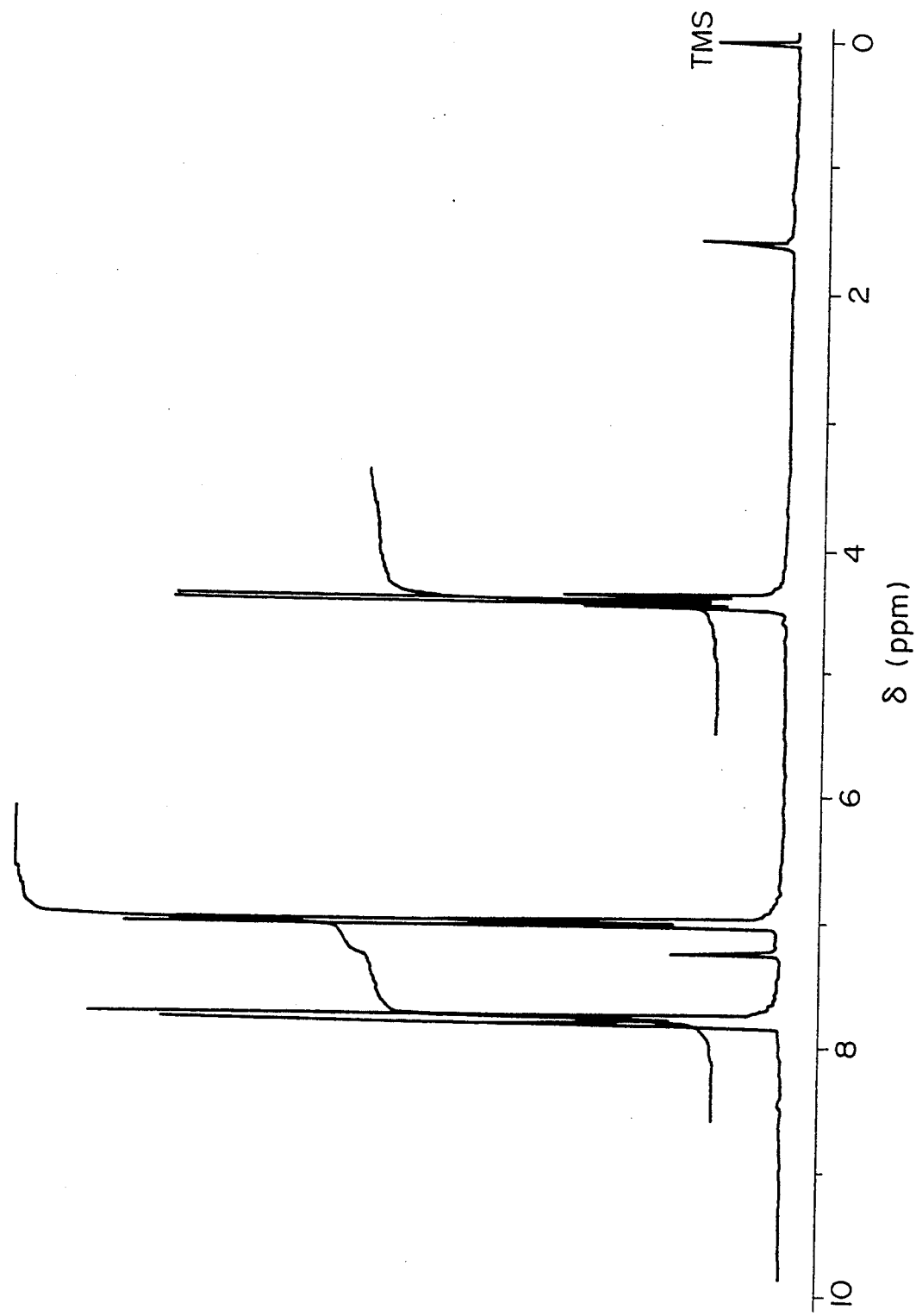
FIG. 2 is a $^1$H-NMR spectrum of 4,4'-bis(2,2,2-trifluoroethoxy)benzophenone.
Figure 3:
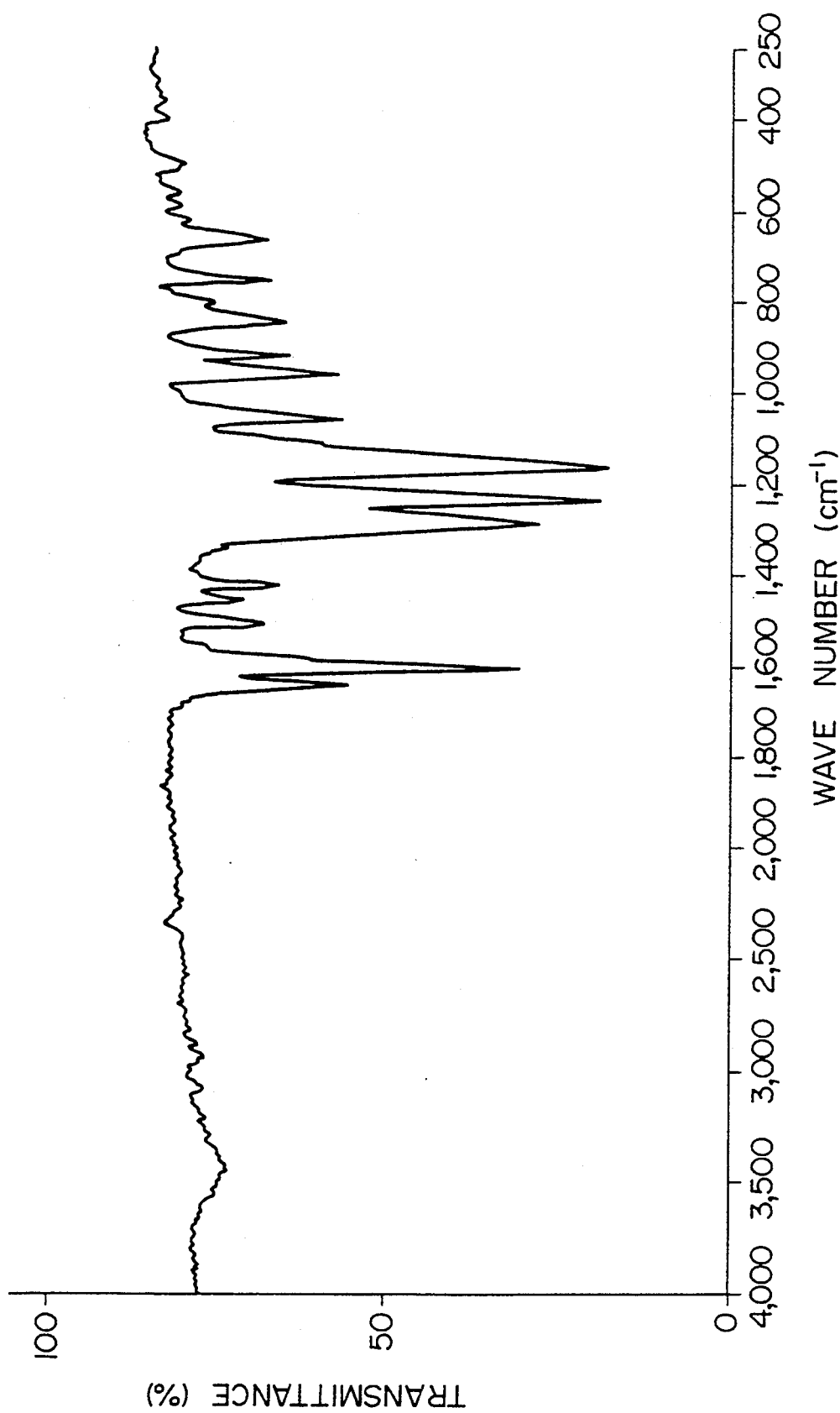
FIG. 3 is an IR spectrum of 4,4'-bis(2,2,2-trifluoroethoxy)benzophenone.

(3) $^{19}$F-NMR ($^{19}$F-NMR spectrum is shown in FIG. 1)
CDCl$_3$ (C$_6$F$_6$ interior standard)
$\delta$value: 87.96 (6F, t, J=8.30 Hz)
(4) $^1$H-NMR ($^1$H-NMR spectrum is shown in FIG. 2)
CDCl$_3$ (TMS interior standard)
$\delta$ values: 7.81 (4H, d, J=8.85 Hz) 7.02 (4H, d, J=8.85Hz) 4.44 (4H, q, J=7.94 Hz)
(5) IR spectrum (KBr method) is shown in FIG. 3.

As shown in FIG. 3, an absorption due to stretching vibration of ketone (>C=O) at near 1610 cm$^{-1}$ and a strong absorption due to stretching vibration of C–F at near 1165 cm$^{-1}$ are found.

These results showed that the objective compound was formed.

EXAMPLE 2

Using the same apparatus as used in Production Example 1, 10 ml of phenyllithium (cyclohexane-diethyl ether solution 2.0 mole/l) was gradually added dropwise to 35 ml of anhydrous THF suspension of 7.25 g (20.5 mmole) of methoxymethyltriphenylphosphorium chloride under a nitrogen atmosphere at room temperature. After stirring at room temperature for 10 minutes, the solution was cooled to −15° C. After adding 40 ml of anhydrous THF of 7.57 g (20.0 mmole) of 4,4'-bis(2,2,2-trifluoroethoxy)benzophenone dropwise for about 25 minutes, the resulting solution was stirred at room temperature for 3 hours. Then, the resulting solution was poured into 600 ml of distilled water and extracted with diethyl ether. After drying, the diethyl ether was distilled off. The resulting brown oily material was purified using an alumina column (benzene: cyclohexane=1:2 by volume) to yield 5.35 g of colorless transparent oily material of 1,1-bis(p-2,2,2-trifluoroethoxyphenyl)-methoxyethylene is yield of 66%.

(1) $^1$H-NMR ($^1$H-NMR spectrum is shown in FIG. 4)
CDCl$_3$ (TMS interior standard)
$\delta$ values: 7.36–6.85 (8H, m)
6.36 (1H, s)

4.34 (4H, q, J=8.24 Hz)
3.75 (3H, s)
These results showed that the objective compound was formed.

EXAMPLE 3

Using a 300-ml flask similar to that used in Production Example 1, 30 ml of diethyl ether solution containing 5.30 g (13.0 mmole) of 1,1-bis(p-2,2,2-triethoxyphenyl)-methoxyethylene was added to 250 ml of acetic acid and 25 ml of 10% sulfuric acid under a nitrogen atmosphere and refluxed for 3.5 hours. After cooling to room temperature, the resulting solution was poured into 500 ml of distilled water, followed by gradual addition of 265 g of sodium carbonate so as to make the solution alkaline. Then, the solution was extracted with diethyl ether, and washed with saturated sodium chloride aqueous solution and distilled water. After drying, the diethyl ether was distilled off to yield 5.04 g of yellow oily 1,1-bis(p-2,2,2-trifluoroethoxyphenyl)acetaldehyde in yield of 98%.

Figure 5:
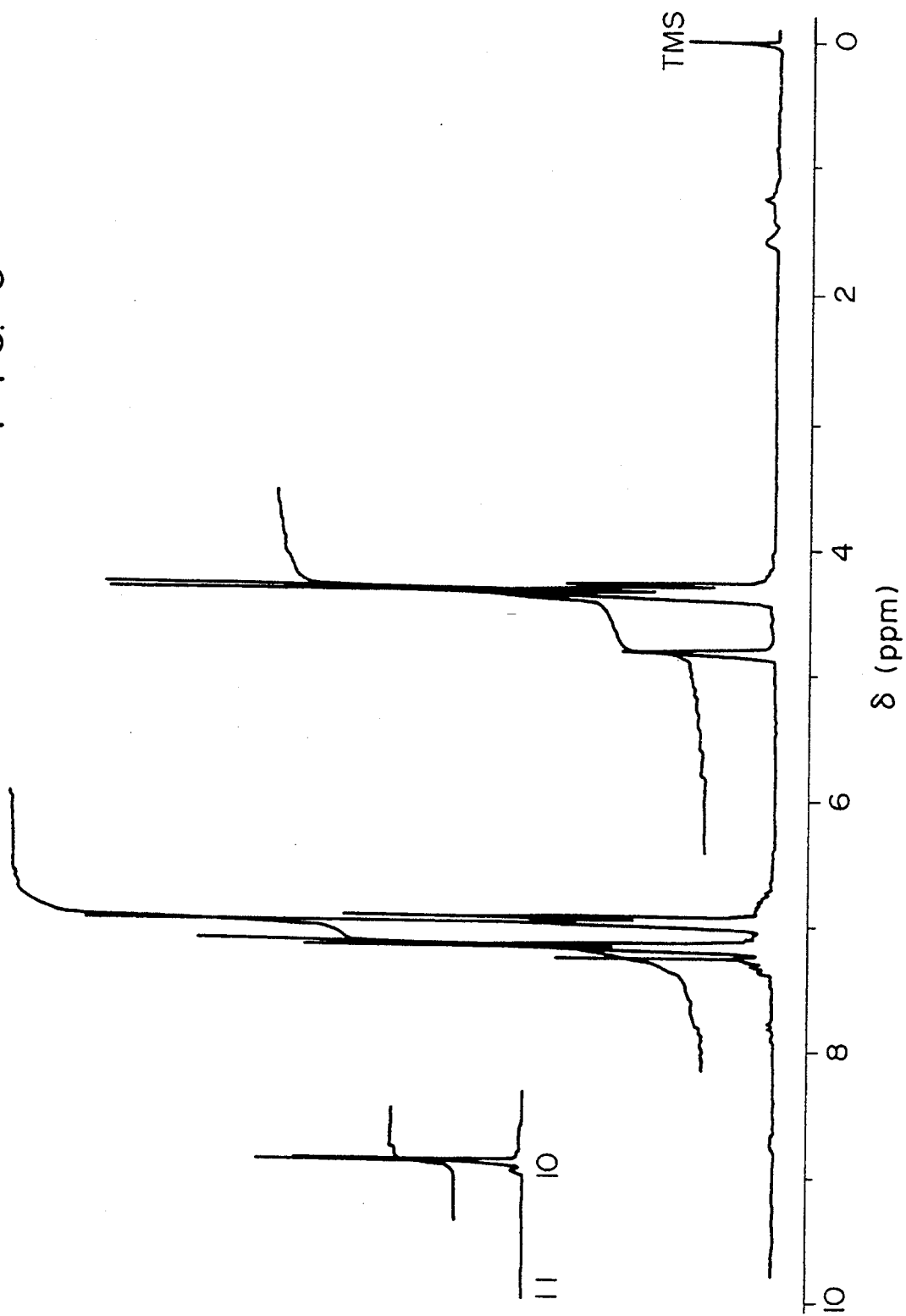
FIG. 5 is a $^1$H-NMR spectrum of 1,1-bis(p-2,2,2-trifluoroethoxyphenyl)acetaldehyde.
Figure 6:
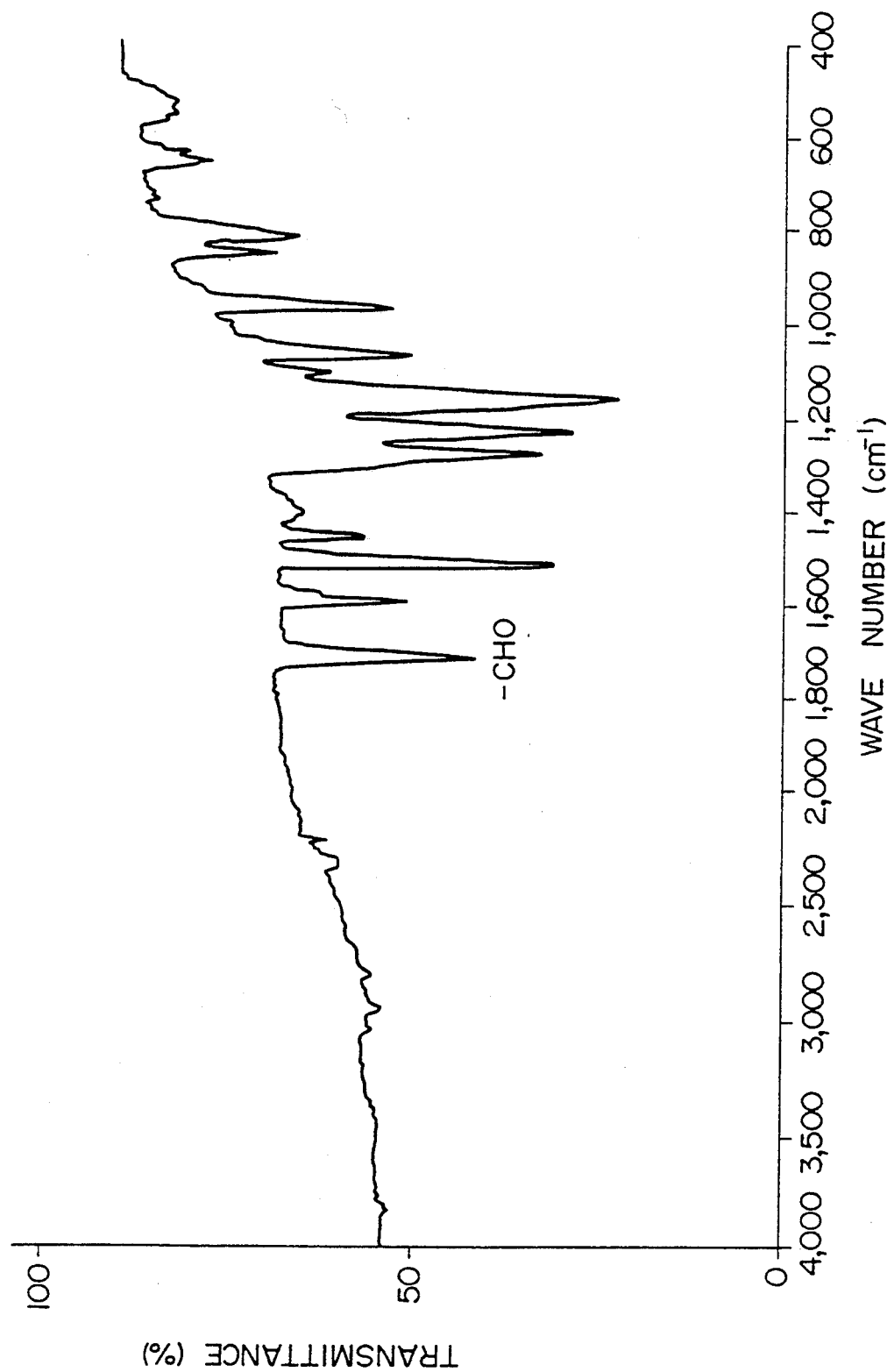
FIG. 6 is an IR spectrum of 1,1-bis(p-2,2,2trifluoroethoxyphenyl)acetaldehyde.

(1) $^1$H-NMR ($^1$H-NMR spectrum is shown in FIG. 5)
CDCl$_3$ (TMS interior standard)
$\delta$ values: 9.89 (1H, d, J=2.13 Hz)
7.17–6.92 (8H, m)
4.83 (1H, d, J=2.14 Hz)
4.34 (4H, q, J=8.24 Hz)
(2) IR spectrum (coating method) is shown in FIG. 6.
As is clear from FIG. 6, an absorption due to aldehyde near about 1720 cm$^{-1}$ is found.
These results showed that the objective compound was found.

EXAMPLE 4

Using a 30-ml flask similar to that use in Production Example 1, 0.49 g (2.90 mmole) of diphenylamine and 5 mg of p-toluenesulfonic acid monohydrate were added to 10 ml of anhydrous toluene solution containing 1.14 g (2.89 mmole) of 1,1-bis(p-2,2,2-trifluoroethoxyphenyl)acetaldehyde under a nitrogen atmosphere and refluxed for 3 hours while dehydrating using molecular sieves 4A. After cooling to room temperature, the resulting solution was filtered and the solvent was distilled off. The residue was purified using an alumina column (toluene: cyclohexane=1:1 by volume). The resulting yellow oily material was recrystallized from n-pentane to give white crystals of 1,1-bis(p-2,2,2-trifluoroethoxyphenyl)-2-(N,N-diphenylamino)ethylene [Compound (3)] in an amount of 1.08 g (yield 67%).

(1) Melting point: 91.0°–93.5° C. (DSC)

|  | (2) Elementary analysis | | |
|---|---|---|---|
|  | C (%) | H (%) | N (%) |
| Calculated | 66.30 | 4.27 | 2.58 |
| Found | 66.17 | 4.07 | 2.54 |

Figure 7:
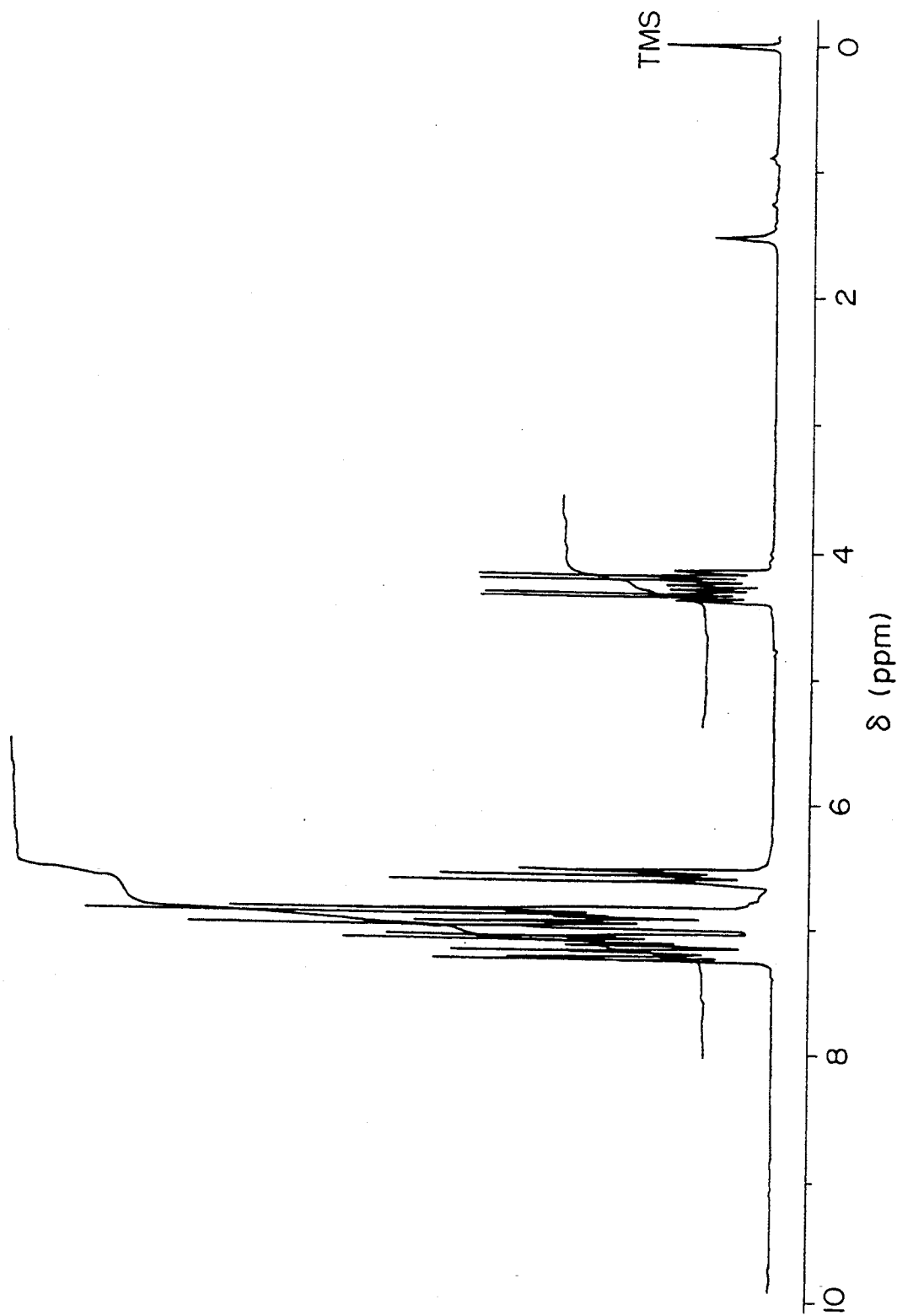
FIG. 7 is a $^1$H-NMR spectrum of 1,1-bis(p-2,2,2-trifluoroethoxyphenyl)-2-(N,N-diphenylamino)ethylene.
Figure 8:
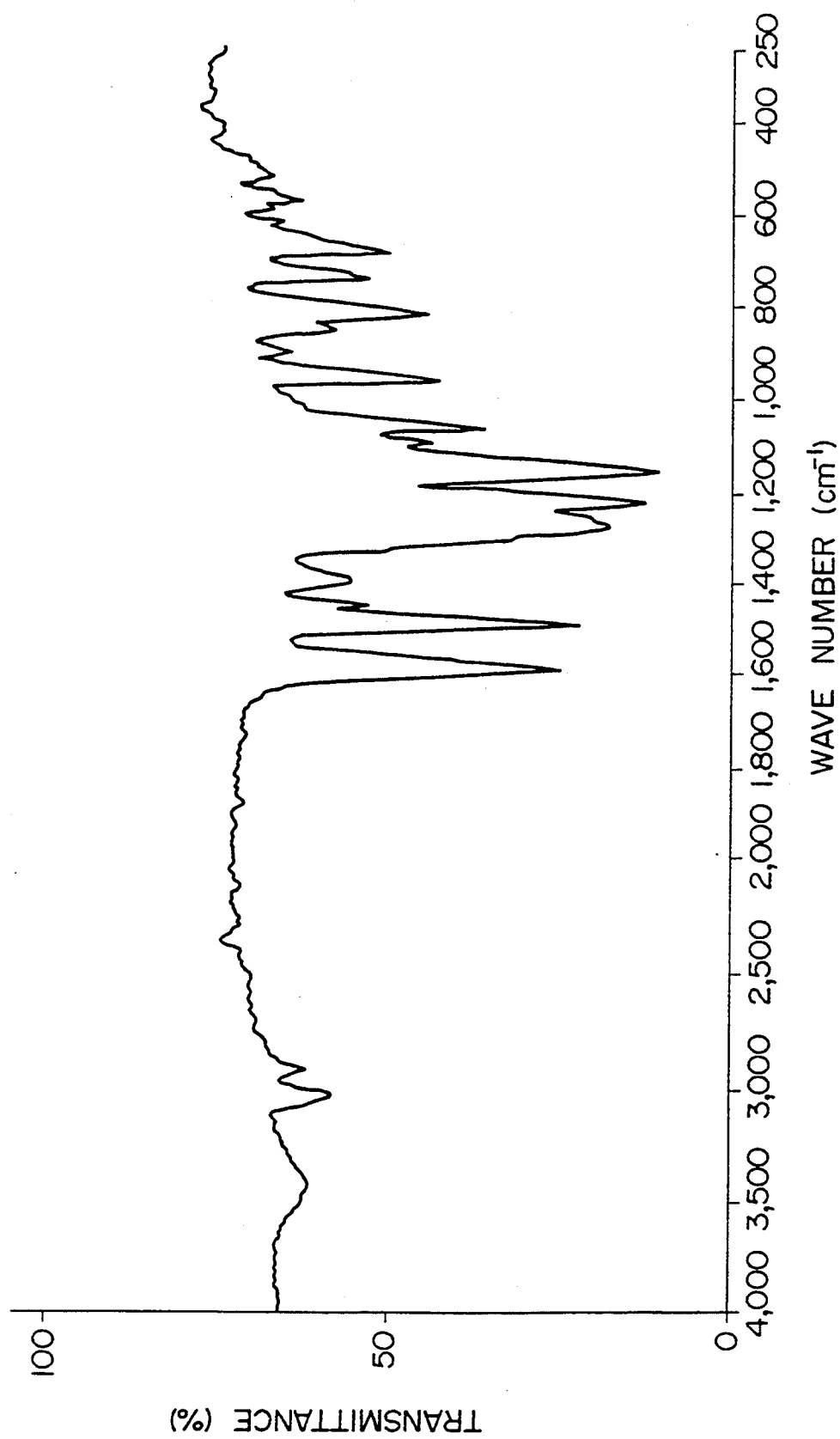
FIG. 8 is an IR spectrum of 1,1-bis(p-2,2,2-trifluoroethoxyphenyl)-2-(N,N-diphenylamino)ethylene.

(3) $^1$H-NMR ($^1$H-NMR spectrum is shown in FIG. 7.)
CDCl$_3$ (TMS interior standard)
$\delta$ value: 7.23–6.84, 6.58–6.54 (18H, m)
6.62 (1H, s)
4.34 (2H, q, J=8.24 Hz)
4.21 (2H, q, J=8.24 Hz)
(4) IR spectrum (KBr method) is shown in FIG. 8.
These results showed that the objective compound was formed.

EXAMPLE 5

Using a 30-ml flask similar to that used in Production Example 1, 0.65 g (2.84 mmole) of 4.4′-dimethoxydiphenylamine and 5 mg of p-toluenesulfonic acid monohydrate were added to 10 ml anhydrous toluene solution containing 1.11 g (2.84 mmole) of 1,1-bis(p-2,2,2-trifluoroethoxyphenylacetaldehyde under a nitrogen atmosphere, and refluxed for 3 hours while dehydrating using molecular sieves 4A. After cooling to room temperature, the solution was filtered and the solvent was distilled off. The residue was purified using an alumina column (toluene). The resulting white solid was recrystallized from hexane to yield white crystals of 1,1-bis(P-2,2,2-trifluoroethoxyphenyl)-2-[N,N-bis(4-methoxyphenyl)amino]ethylene [Compound (4)] in an amount of 1.46 g (yield 85%).

(1) Melting point: 86.5°–89.0° C.

|  | (2) Elementary analysis | | |
|---|---|---|---|
|  | C (%) | H (%) | N (%) |
| Calculated | 63.68 | 4.51 | 2.32 |
| Found | 63.59 | 4.39 | 2.26 |

Figure 9:
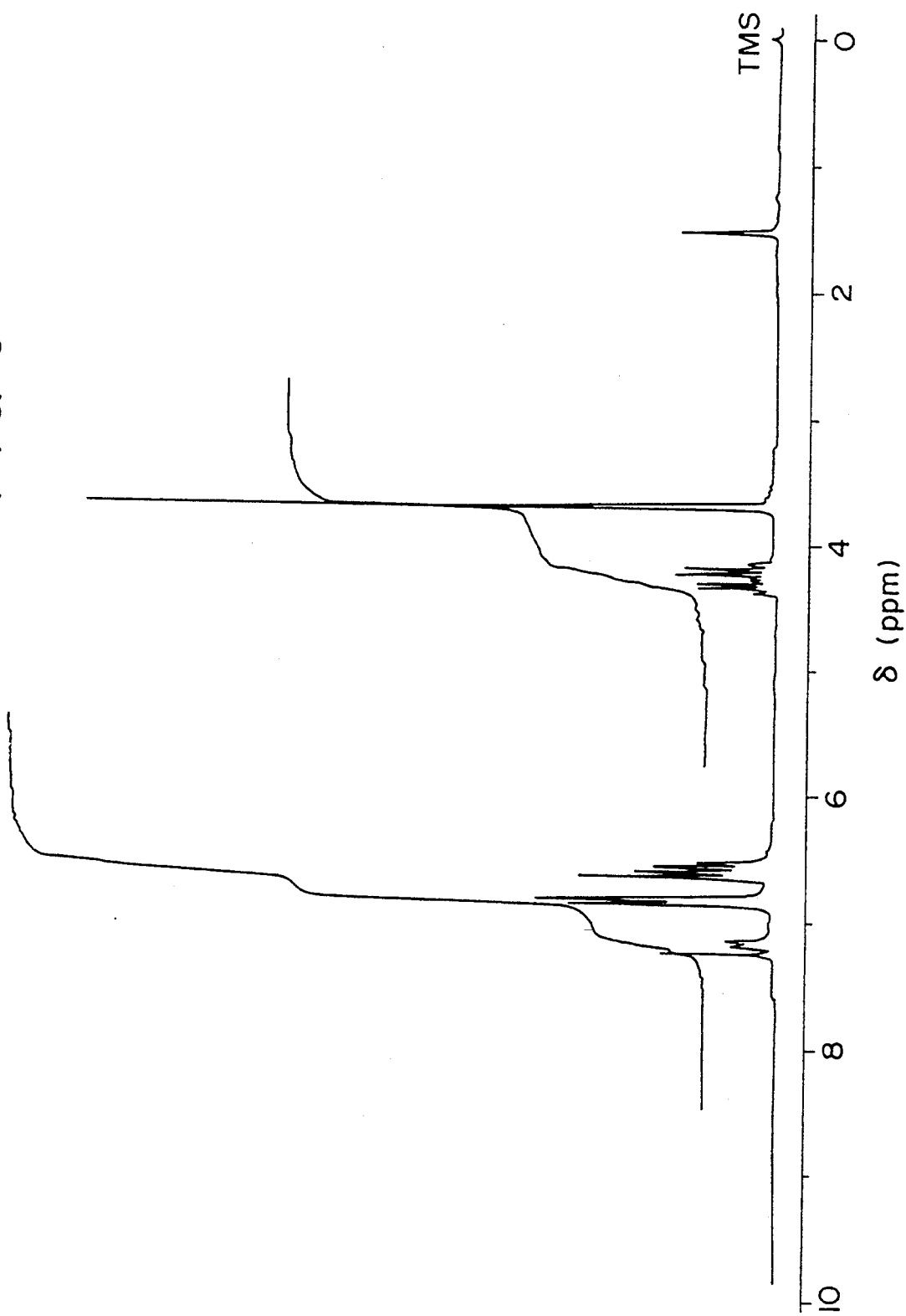
FIG. 9 is a $^1$H-NMR spectrum of 1,1-bis(p-2,2,2-trifluoroethoxyphenyl)-2-[N,N-bis(4-methoxyphenylamino]ethylene.
Figure 10:
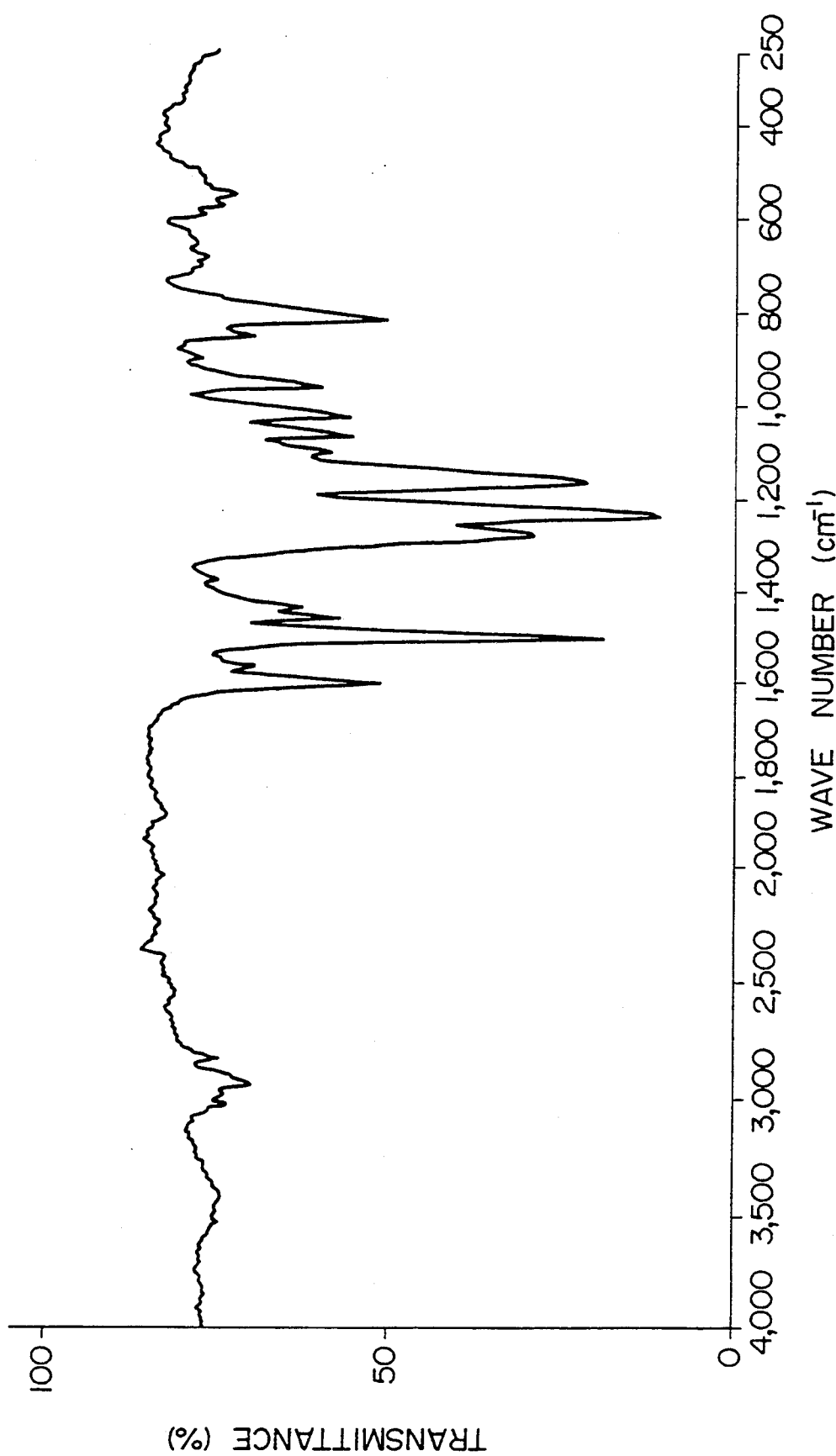
FIG. 10 is an IR spectrum of 1,1-bis(p-2,2,2-trifluoroethoxyphenyl)-2-[N,N-bis(4-methoxyphenyl)amino]ethylene.

(3) $^1$H-NMR ($^1$H-NMR spectrum is shown in FIG. 9.)
CDCl$_3$ (TMS interior standard)
$\delta$ values 7.25–6.52 (17H, m)
4.33 (2H, q, J=8.24 Hz)
4.21 (2H, q, J=8.24 Hz)
3.71 (6H, s)
(4) IR spectrum (KBr method) is shown in FIG. 10.
These results showed that the objective compound was formed.

EXAMPLE 6

Using a 30-ml flask similar to that used in Production Example 1, 0.56 g (2.85 mmole) of p,p′-ditolylamine and 5 mg of p-toleuensulfonic acid monohydrate were added to 10 ml of anhydrous toluene solution containing 1.12 g (2.85 mmole) of 1,1-bis(p-2,2,2-trifluoroethoxyphenyl)acetaldehyde under a nitrogen atmosphere, and refluxed for 3 hours while dehydrating using molecular sieves 4A. After cooling to room temperature, the resulting solution was filtered and the solvent was distilled off. The residue was purified using an alumina column (toluene: cyclohexane=1:2 by volume). The resulting pale yellow oily material was recrystallized from hexane to yield white crystals of 1,1-bis(p-2,2,2-trifluoroethoxyphenyl)-2-[N,N-bis(4-methylphenyl)amino]ethylene [Compound (5)] in an amount of 1.24 g (yield 77%).

(1) Melting point: 117.5°–119.5° C.

|  | (2) Elementary analysis | | |
|---|---|---|---|
|  | C (%) | H (%) | N (%) |
| Calculated | 67.25 | 4.76 | 2.45 |
| Found | 67.14 | 4.70 | 2.39 |

Figure 11:
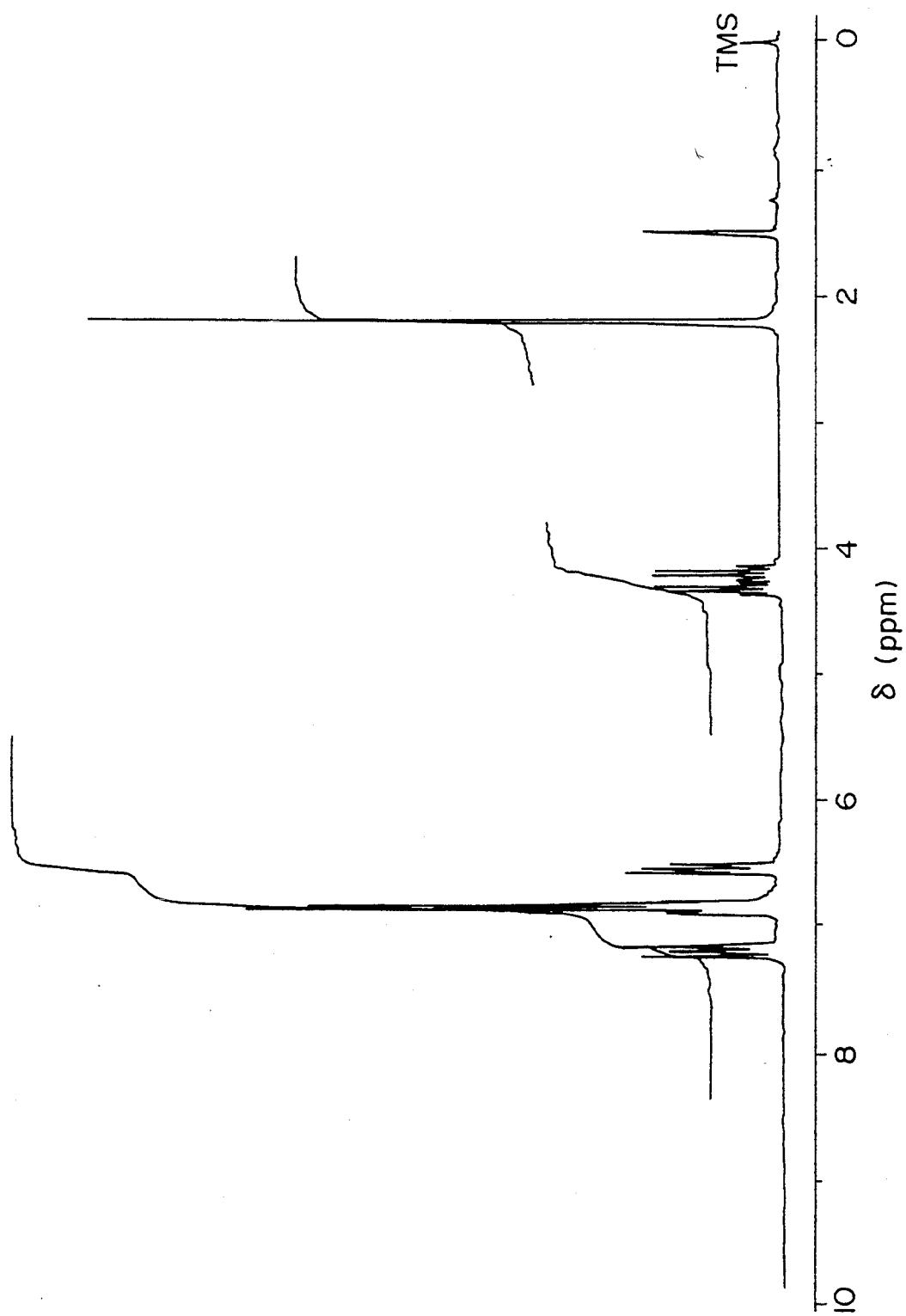
FIG. 11 is a $^1$H-NMR spectrum of 1,1-bis(p-2,2,2-trifluoroethoxyphenyl)-2-[N,N-bis(4-methylphenyl)amino]ethylene.

(3) $^1$H-NMR ($^1$H-NMR spectrum is shown in FIG. 11.)
CDCl$_3$ (TMS interior standard)
$\delta$ values: 7.20–6.52 (17H, m)
4.33 (2H, q, J=8.24 Hz)
4.21 (2H, q, J=8.24 Hz)
2.21 (6H, S)

Figure 12:
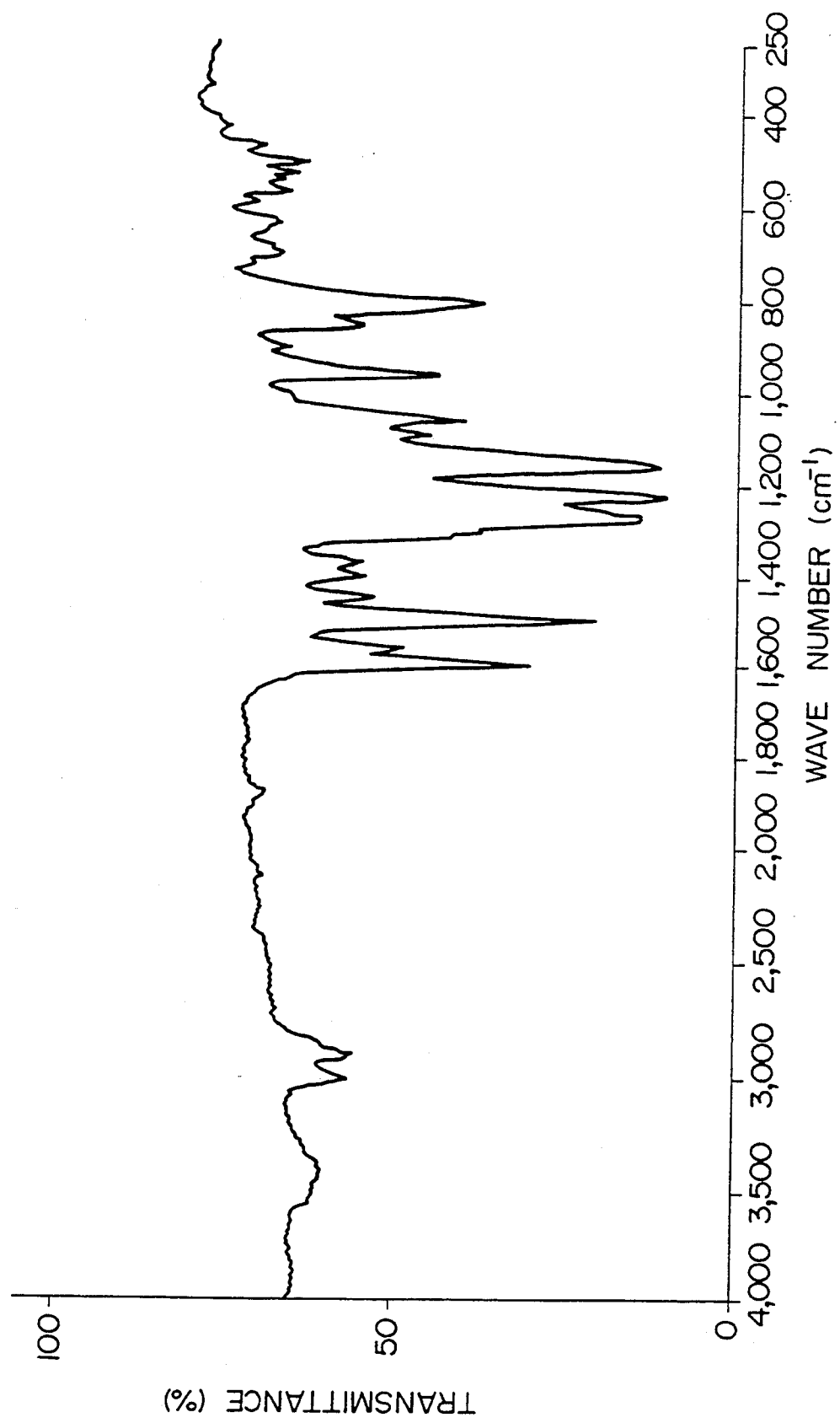
FIG. 12 is an IR spectrum of 1,1-bis(p-2,2,2-trifluoroethoxyphenyl)-2-[N,N-bis(4-methylphenyl)amino]ethylene.

(4) IR spectrum (KBr method) is shown in FIG. 12.
These results showed that the objective compound was formed.

EXAMPLE 7

Using a 30-ml flask similar to that used in Production Example 1, 0.62 g (2.85 mmole) of N-phenyl-2-naphthylamine and 5 ml of p-toluenesulfonic acid monohydrate were added to 10 ml anhydrous toluene solution containing 1.12 g (2.85 mmole) of 1.1-bis(p-2,2,2-trifluoroethoxyphenyl)acetaldehyde under a nitrogen atmosphere, and refluxed for 3 hours while dehydrating using molecular sieves 4A. After cooling to room temperature, the resulting solution was filtered and the solvent was distilled off. The residue was purified using alumina column (toluene: cyclohexane=1:1 by volume). The resulting pale yellow oily material was recrystallized from hexane to yield yellow crystals of 1,1-bis(p-2,2,2-trifluoroethoxyphenyl)-2-(N-phenyl-N-2-naphthylamine)ethylene [Compound (6)] in an amount of 1.34 g (yield 79%).

(1) Melting point: 102.0°–104.0° C.

|  | (2) Elementary analysis | | |
|---|---|---|---|
|  | C (%) | H (%) | N (%) |
| Calculated | 68.80 | 4.25 | 2.36 |
| Found | 6B.80 | 4.18 | 2.30 |

Figure 13:
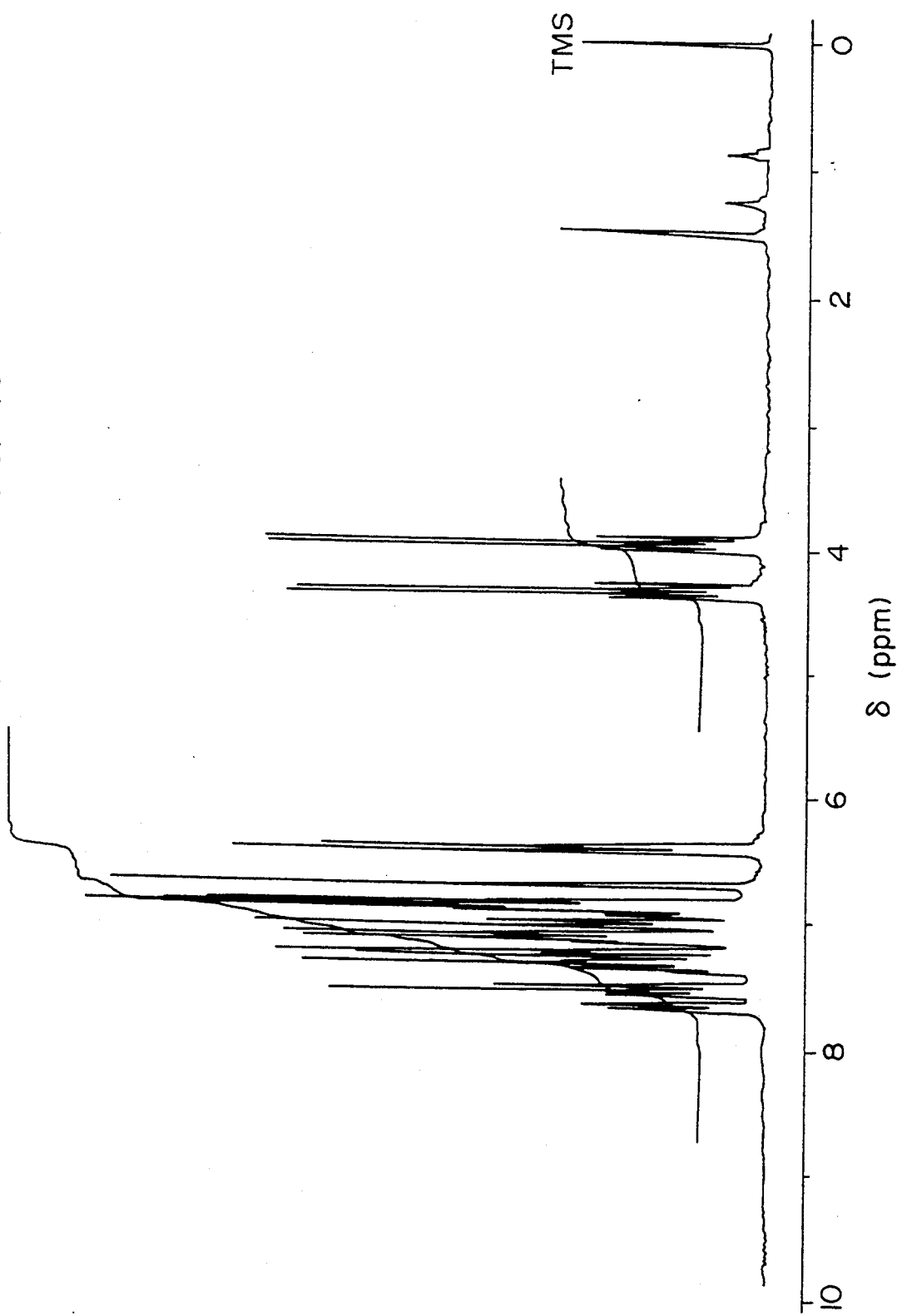
FIG. 13 is a $^1$H-NMR spectrum of 1,1-bis(p-2,2,2-trifluoroethoxyphenyl)-2-(N-phenyl-N-2-naphthylamino)ethylene.
Figure 14:
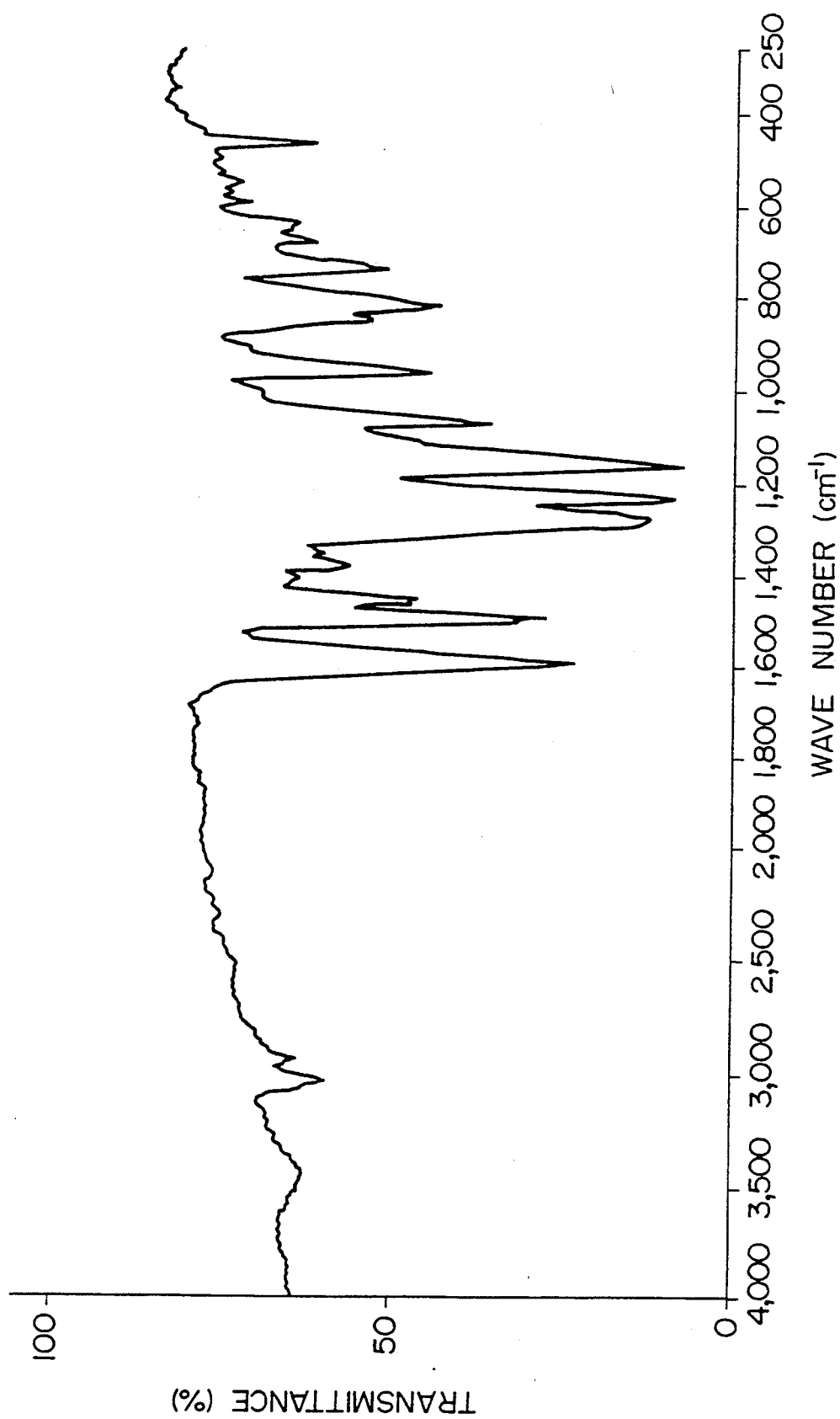
FIG. 14 is an IR spectrum of 1,1-bis(p-2,2,2-trifluoroethoxyphenyl)-2-(N-phenyl-N-2-naphthylamino)ethylene.

(3) $^1$H-NMR ($^1$H-NMR spectrum is shown in FIG. 13.)
CDCl$_3$ (TMS interior standard)
δ values: 7.68–6.83, 6.45–6.41 (20H, m)
6.72 (1H, s)
4.35 (2H, q, J=8.24 Hz)
3.96 (2H, q, J=8.24 Hz)
(4) IR spectrum (KBr method) is shown in FIG. 14.
These results showed that the objective compound was formed.

EXAMPLES 8 TO 13

A liquid was prepared by dispersing 1 part of τ-form non-metallic phthalocyanine (mfd. by Toyo Ink Manufacturing Co., Ltd.) in 6.7 parts of silicone resin (KR 5240, a trade name, mfd. by Shi-etsu Chemical Industry Co., Ltd.) and tetrahydrofuran so as to make a 5% liquid. The resulting liquid was ball milled for 5 hours using a ball mill pot having a diameter of about 9 cm (mfd. by Nippon Kagaku Togyo K. K.). The resulting pigment dispersed liquid was coated on an aluminum plate (0.1 mm thick) using an applicator, and dried at 90° C. for 40 minutes to form a charge generation layer of 0.5 μm thick.

Then, 1 part of enamine derivative of the formula (I) shown in Table 1 and 3.0 parts of polycarbonate resin (Lexan 141, a trade name, mfd. by General Electric Company) were dissolved in a mixed solvent of methylene chloride and 1,2-dichloroethane (1:1 by weight) to give a 17% solution. The resulting solution was coated on the charge generation layer using an applicator and dried at 100° C. for 40 minutes to form a change transport layer of 18 μm thick. Thus, an electrophotographic member was prepared.

Electrophotographic properties of electrophotographic members obtained as mentioned above were measured using an electrostatic recording paper analyzer (SP-428, mfd. by Kawaguchi Electric Works Co., Ltd.) and shown in Table 1.

In Table 1, the potential $V_0$ (—V) means a charging potential when the electrophotographic member was subjected to corona discharge of —5 kV for 10 seconds in the dynamic measurement, the dark decay ($V_k$) means a potential maintaining ratio from the potential ($V_{30}$) when allowed to stand in the dark for 30 second thereafter [($V_{30}/V_0$)×100%], and the half decay exposure amount ($E_{50}$) means a light amount until the potential becomes half of $V_{30}$ when exposed to white light of 10 lux. The residual potential ($V_R$) means a surface potential after exposed to white light of 10 lux for 30 seconds.

TABLE 1

| Example No. | Formula (I), (k = 0, m = 1, n = 1) | | | $V_0$ (—V) | $V_k$ (%) | $E_{50}$ (lux · sec) | $V_R$ (—V) |
|---|---|---|---|---|---|---|---|
|  | $R_1$ | $R_2$ | $R_3$ |  |  |  |  |
| Example 8 | (CF$_3$CF$_2$)$_2$N— | —⟨phenyl⟩ | —⟨phenyl⟩ | 710 | 81.0 | 1.4 | 0 |
| Example 9 | CF$_3$CH$_2$O— | —⟨phenyl⟩ | —⟨phenyl⟩ | 700 | 83.5 | 1.3 | 0 |
| Example 10 | CF$_3$CH$_2$O— | —⟨phenyl⟩—OCH$_3$ | —⟨phenyl⟩—OCH$_3$ | 720 | 84.2 | 1.2 | 0 |
| Example 11 | CF$_3$CF$_3$CF$_2$O— | —⟨phenyl⟩—CH$_3$ | —⟨phenyl⟩—CH$_3$ | 740 | 81.7 | 1.4 | 0 |

TABLE 1-continued

| Example No. | Formula (I), (k = 0, m = 1, n = 1) | | | $V_0$ (−V) | $V_k$ (%) | $E_{50}$ (lux·sec) | $V_R$ (−V) |
| --- | --- | --- | --- | --- | --- | --- | --- |
| | $R_1$ | $R_2$ | $R_3$ | | | | |
| Example 12 | $CF_3CF_2CH_2O-$ | phenyl | phenyl | 700 | 82.7 | 1.2 | 0 |
| Example 13 | $(CF_3CF_2CH_2)_2N-$ | phenyl | naphthyl | 730 | 82.4 | 1.2 | 0 |

EXAMPLES 14 TO 16

Electrophotographic members were produced in the same manner as described in Example 10 except for using the enamine derivative of the formula (I) as listed in Table 2 and Lexan in the mixing ratio as listed in Table 2. Electrophotographic properties of the resulting electrophotographic members were measured and shown in Table 2.

COMPARATIVE EXAMPLES 1 TO 4

Electrophotographic members were produced in the same manner as described in Examples 14 to 16 except for using the enamine derivatives of the formula (I) but containing no fluorine atoms as listed in Table 2. Electrophotographic properties of the resulting electrophotographic members were measured and shown in Table 2.

TABLE 2

| Example No. | Formula (I), (k = 0, m = 1, n = 1) | | | Enamine derivative/ binder (wt. ratio) | $E_{50}$ (lux·sec) | $V_R$ (−V) |
| --- | --- | --- | --- | --- | --- | --- |
| | $R_1$ | $R_2$ | $R_3$ | | | |
| Example 10 | $CF_3CH_2O-$ | $-C_6H_4-OCH_3$ | $-C_6H_4-OCH_3$ | 1/3.0 | 1.2 | 0 |
| Example 14 | $CF_3CH_2O-$ | $-C_6H_4-OCH_3$ | $-C_6H_4-OCH_3$ | 1/2.3 | 1.2 | 0 |
| Example 15 | $CF_3CH_2O-$ | $-C_6H_4-OCH_3$ | $-C_6H_4-OCH_3$ | 1/1.9 | 1.1 | 0 |
| Example 16 | $CF_3CH_2O-$ | $-C_6H_4-OCH_3$ | $-C_6H_4-OCH_3$ | 1/1.5 | 1.0 | 0 |
| Comparative Example 1 | $CH_3CH_2O-$ | $-C_6H_4-OCH_3$ | $-C_6H_4-OCH_3$ | 1/3.0 | 1.6 | 0 |
| Comparative Example 2 | $CH_3CH_2O-$ | $-C_6H_4-OCH_3$ | $-C_6H_4-OCH_3$ | 1/2.3 | 1.5 | 0 |
| Comparative Example 3 | $CH_3CH_2O-$ | $-C_6H_4-OCH_3$ | $-C_6H_4-OCH_3$ | 1/1.9 | 1.4 | 5 |
| Comparative Example 4 | $CH_3CH_2O-$ | $-C_6H_4-OCH_3$ | $-C_6H_4-OCH_3$ | 1/1.5 | 1.4 | 5 |

COMPATIBILITY TEST

The charge transport layers in amounts of about 8 mg were cut off from the electrophotographic members obtained in Example 16 and Comparative Example 4 and subjected to thermal analysis using a differential thermal analyzer (Model 9900 mfd. by E. I. du Pont de Nemours & Co., Inc.).

As a result, the sample of Example 16 showed only the glass transition point (62° C.) of a mixed phase of the binder and the enamine derivative, and showed no melting point of enamine derivative (86.5° to 89.0° C.) and no glass transition point of the binder (147° C). It was confirmed that no phase separation of the charge transport material and the binder took place and the charge transport layer showing excellent compatibility was formed.

In contrast, the sample of Comparative Example 4 showed a small peak at 147° C. due to the glass transition point (147° C.) of the binder and a peak at 75° C. due to the glass transition point of a mixture of the binder and the enamine derivative. It was confirmed that the enamine derivative and the binder were not compatible microscopically and the change transport layer phase separated microscopically was formed.

Figure 15:
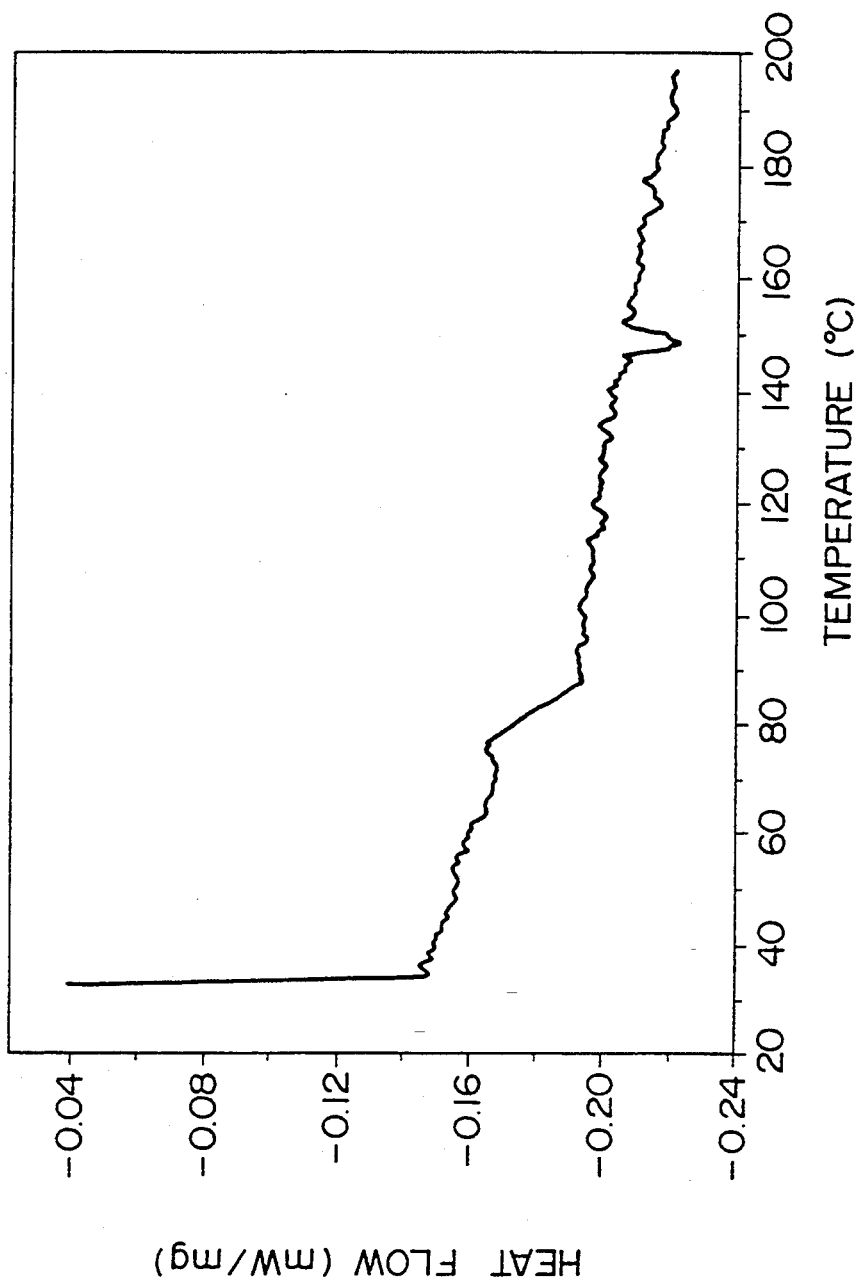
FIG. 15 is a differential scanning calorimetry chart of a charge transport layer containing an enamine derivative including no fluorine-containing substituent.
Figure 16:
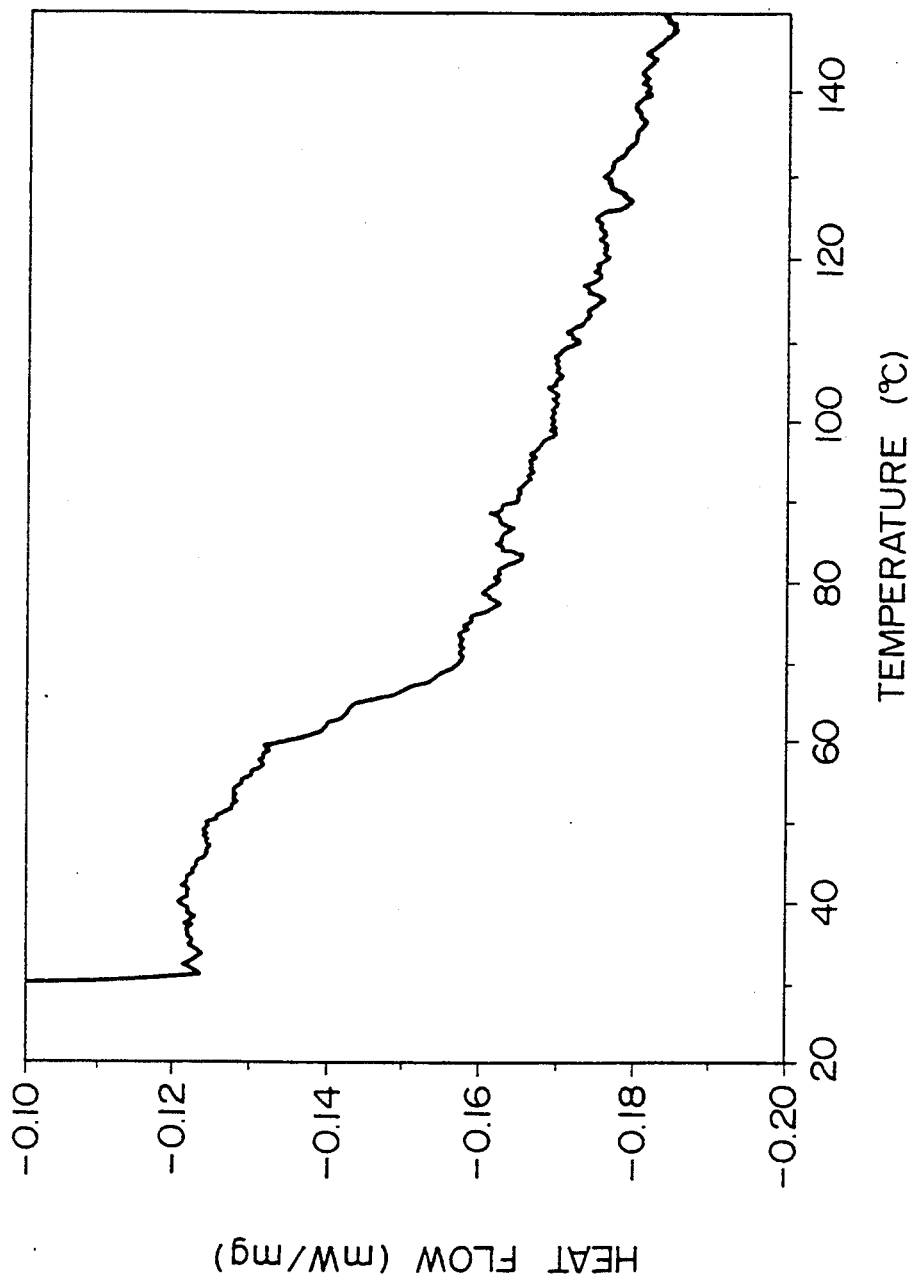
FIG. 16 is a differential scanning calorimetry chart of a charge transport layer containing an enamine derivative including fluorine-containing substituents.

FIG. 15 shows a differential scanning calorimetry chart of Comparative Example 4 and FIG. 16 shows that of Example 16.

As mentioned above, the enamine derivatives of the present invention are compounds remarkably excellent in solubility in organic solvent and/or binders. Thus, electrophotographic members using such enamine derivatives have very excellent electrophotographic properties such as high sensitivity, low recidual potential, high durability, etc.

What is claimed is:

1. An enamine derivative of the formula:

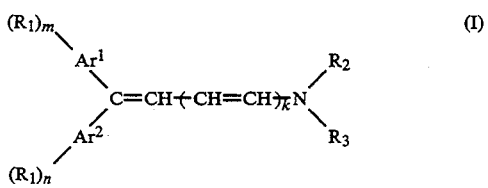

wherein $R_1$ is a fluorine-containing substituent of the formula RfO— or (Rf)$_2$N—; Rf is a fluoroalkyl group, a fluoroaryl group or a fluoroaralkyl group; a plurality of $R_1$ may be the same or different; $R_2$ and $R_3$ are independently an alkyl group, an aryl group, an aralkyl group, an alicyclic group, a heterocyclic group, or a residual group necessary for for forming a 5-membered or 6-membered ring by combining $R_2$ and $R_3$, these groups of $R_2$ and $R_3$ being able to have one or more substituents; $Ar^1$ and $Ar^2$ are independently an aryl group or arylene group which may have one or more substituents other than $R_1$; k is zero or an integer of 1; and m and n are independently zero or an integer of 1 to 3, provided that m and n cannot be zero at the same time.

2. An enamine derivative according to claim 1, which is represented by the formula:

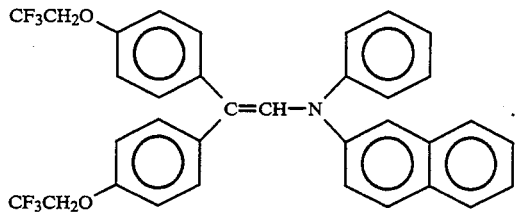

3. An enamine derivative according to claim 1, which is represented by the formula:

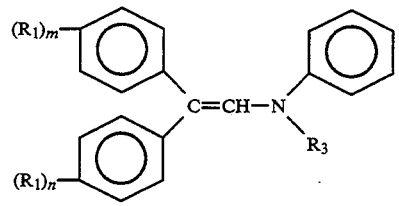

wherein $R_1$ is CF$_3$CG$_2$O—, CF$_3$CF$_2$CH$_2$O—, (CF$_3$CH$_2$)$_2$N—, or (CF$_3$CF$_2$CH$_2$)$_2$N—, a plurality of $R_1$ may be the same or different; m and n are independently zero or 1, provided that m and n cannot be zero at the same time; and $R_3$ is

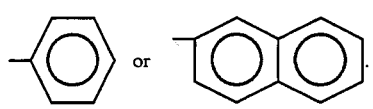

4. An enamine derivative according to claim 1, which is represented by the formula:

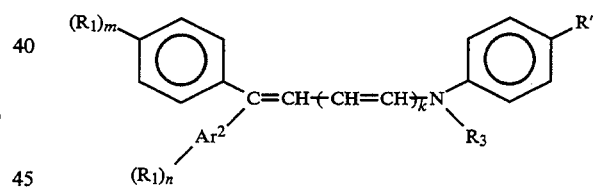

wherein $R_1$ is CF$_3$CH$_2$O—, CF$_3$CF$_2$CH$_2$O—, (CF$_3$CH$_2$)$_2$N—, or (CF$_3$CF$_2$CH$_2$)$_2$N—, a plurality of $R_1$ may be the same or different; m and n are independently zero or 1, provided that m and n cannot be zero at the same time; R' is hydrogen, methoxy or methyl and $R_3$ is

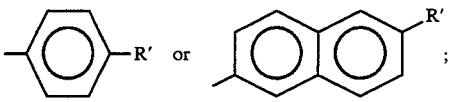

$Ar^2$ is

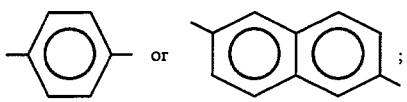

and k is zero or an integer of 1.

* * * * *